United States Patent [19]

Buténas et al.

[11] Patent Number: 5,399,487
[45] Date of Patent: Mar. 21, 1995

[54] 6-PEPTIDYLAMINO-1-NAPHTHALENESULFONAMIDES USEFUL AS FLUOROGENIC PROTEOLYTIC ENZYME SUBSTRATES

[75] Inventors: Saulius Buténas, Burlington, Vt.; Jeffrey H. Lawson, Durham, N.C.; Kenneth G. Mann, Shelburne, Vt.

[73] Assignee: Haematologic Technologies, Inc., Essex Jct., Vt.

[21] Appl. No.: 27,294

[22] Filed: Mar. 4, 1993

[51] Int. Cl.⁶ .............. C12Q 1/56; C12Q 1/00; C07D 273/04; C07D 257/08
[52] U.S. Cl. .......................... 435/13; 435/4; 514/19; 514/20; 514/183; 514/319; 514/822; 544/67; 544/88; 544/179; 544/145
[58] Field of Search ............ 435/13, 4; 514/19, 822, 514/20, 319, 183, 145; 424/244, 177; 546/145; 544/67, 88, 179, 145

[56] References Cited

U.S. PATENT DOCUMENTS

| | | | |
|---|---|---|---|
| 3,884,896 | 5/1975 | Blomback et al. | 435/13 |
| 3,886,136 | 5/1975 | Claeson et al. | 435/13 |
| 4,001,087 | 11/1977 | Wong et al. | 435/13 |
| 4,018,915 | 4/1977 | Okamoto et al. | 424/177 |
| 4,036,955 | 7/1977 | Okamoto | 424/177 |
| 4,154,828 | 5/1979 | Okamoto et al. | 424/244 |

OTHER PUBLICATIONS

Butenas et al, Biochem 31: 5399–5411, 1992.
Okamoto et al, Chem. Abstracts 86(21): 155972t (1977).
Chem. Abstracts, 109: 110461c (1988).
Chem. Abstracts. 62: 1615b and c (1965).
Chem. Abstracts, 51: 4722a (1957).
Lottenberg et al., Methods Enzymol., 80, 341–361, 1981.
Bell et al., Anal. Biochem., 61, 200–208, 1974.
Nieuwenhuizen et al., Anal. Biochem., 83, 143–148, 1977.
Morita et al., J. Biochem., 82, 1495–1498, 1977.
Cho et al., Biochemistry, 23, 644–50, 1984.
McRae et al., Biochemistry, 20, 7196–7206, 1981.
Lawson and Mann, J. Biol. Chem., 266: 11317–11327, 1991.
Lawson et al., J. Biol. Chem. 267: 4834–4843, 1992.
Butenas et al., Biochem. 31: 5399–5311, 1992.
Butenas et al., Chemistry, [Lithuanian Academy of Sciences] 182: 144–153, 1992.

Primary Examiner—Michael G. Wityshyn
Assistant Examiner—Louise N. Leary
Attorney, Agent, or Firm—Allegretti & Witcoff, Ltd.

[57] ABSTRACT

The present invention encompasses compounds of formula I:

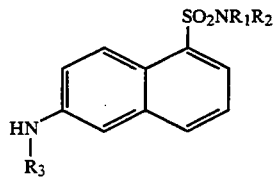

and the pharmaceutically acceptable non-toxic salts thereof; wherein
$R_1$ is hydrogen, lower alkyl, alkenyl, alkynyl, cycloalkyl, alkylcycloalkyl, cycloalkylalkyl, or phenylalkyl;
$R_2$ is hydrogen, alkyl, alkenyl, alkynyl, cycloalkyl, alkylcycloalkyl, cycloalkylalkyl, or phenylalkyl; or $NR_1R_2$ forms a nitrogen heterocycle; and
$R_3$ is hydrogen, an amino acid or a peptide residue.

These compounds may be employed as substrates in assays for determining proteolytic enzyme activity or as enzyme inhibitors. The invention also encompasses methods for determining proteolytic enzyme activity using the compounds of formula I.

38 Claims, 3 Drawing Sheets

6-PEPTIDYLAMINO-1-NAPHTHALENESUL-FONAMIDES USEFUL AS FLUOROGENIC PROTEOLYTIC ENZYME SUBSTRATES

BACKGROUND OF THE INVENTION

1. Field of the Invention

The present invention relates to (1) novel 6-peptidylamino-1-naphthalenesulfonamides and (2) novel 6-amino-1-naphthalenesulfonamides. More particularly, the invention relates to novel 6-peptidylamino-1-naphthalenesulfonamides which are fluorogenic substrates for proteolytic enzymes, and specifically for the proteases involved in fibrinolysis and blood coagulation. These compounds are useful as substrates for determining proteolytic enzyme activity and as inhibitors of the enzymes. The invention also relates to 6-amino-1-naphthalenesulfonamide which are fluorogenic products of a reaction between a proteolytic enzyme and a 6-peptidylamino-1-naphthalensulfonamide substrate.

2. Description of the Related Art

Many of the proteases involved in blood coagulation and fibrinolysis can be described as trypsin-like in that they are serine proteases which preferentially hydrolyze peptide, ester, or amide bonds in which a basic amino acid provides the carbonyl group of the scissile bond. The in vivo specificity of these enzymes is a complex function of a variety of structural factors including binding domains in the protease for specific amino acid side chains located on both the amino and carboxyl side of the targeted lysine or arginine residue in the substrate protein. The idea that short peptide substrates can be designed to incorporate enough information to discriminate among these proteases relies on the concept that each active site is comprised of a unique series of side chain binding pockets.

Many fluorogenic and chromogenic amino acid substrates for proteolytic enzymes have been reported for assaying proteases. Lottenberg et al., (Methods Enzymol., 80, 341–361, 1981) report kinetic data for a large number of peptide derivative protease substrates. These substrates included p-nitroanilide (4-nitroanilide) derivatives, thiobenzyl esters, and nitrobenzyl esters of peptide residues having arginine or lysine at the carboxy terminus. Data were also presented for 7-amino-4-methylcoumarin, 2-naphthylamide (β-naphthylamide), and 5-aminoisophthalic acid peptide derivatives. The derivatives, where P represents a peptide attached via the carbonyl of its carboxy terminus, may be represented as follows:

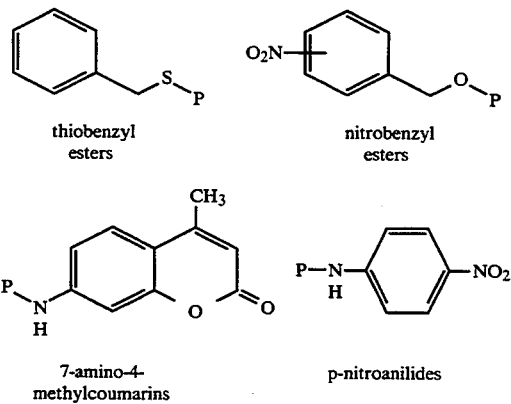

thiobenzyl esters nitrobenzyl esters 7-amino-4-methylcoumarins p-nitroanilides

-continued

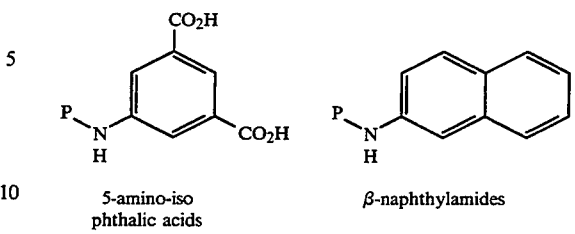

5-amino-iso phthalic acids

β-naphthylamides

Bell et al., (Anal. Biochem., 61, 200–208, 1974) reported a fluorometric assay for plasmin, plasminogen, and streptokinase using α-N-methyl, α-N-tosyl-L-lysine ester of β-naphthol.

Nieuwenhuizen et al., (Anal. Biochem., 83, 143–148, 1977) analyzed β-naphthylamide derivatives of peptides having arginine at the carboxy terminus for their use as substrates of plasmin, urokinase, and plasminogen activator.

Morita et al., (J. Biochem., 82, 1495–1498, 1977) examined peptide-4-methylcoumarins containing arginine at the carboxy terminus as substrates for α-thrombin, factor Xa, and kallikreins, urokinase, and plasmin.

Cho et al., (Biochemistry, 23, 644–650, 1984) used a series of tripeptide 4-nitroanilide substrates in mapping studies of the $S_3$ subsite of several serine proteases involved in blood coagulation. These substrates were of the type Z-AA-Gly-Arg-NA and Z-AA-PHE-ARG-NA where AA represents an amino acid and NA is 4-nitroanilide.

McRae et al., (Biochemistry, 20, 7196–7206, 1981) mapped the subsite specificities of certain proteases using amino acid, dipeptide, and longer peptide thioester substrates.

Chem. Abstracts, 109: 110461c [Japanese patent No. 63017870 A2 (Hidaka et al.)] discloses hexahydro-1-(naphthylsulfonyl)-1H-1,4-diazepines as cardiovascular agents. The disclosed compounds have the formula:

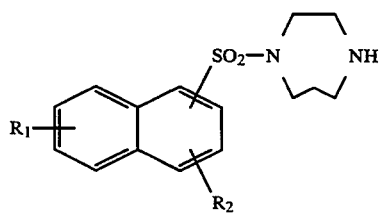

where $R_1$ and $R_2$ represent H, halogen, lower alkyl, lower alkoxy, OH, $NH_2$, lower alkylamino, lower acylamino, $NO_2$, and cyano.

Chem. Abstracts. 62: 1615b and c [Polish patent application No. 48,252 (Wojtkiewicz and Jankowski, 1963)] discloses the synthesis of sulfonamide derivatives of 2-naphthylamine, including 2-aminonaphthalene-5-sulfonamide(i, R,R'=H), 2-aminonaphthalene-5-(N-methyl)sulfonamide(i, R=$CH_3$, R'=H), and 2-aminonaphthalene-5-(N,N-dimethyl)sulfonamide(i, R,R'=$CH_3$).

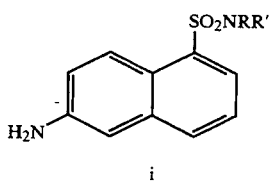

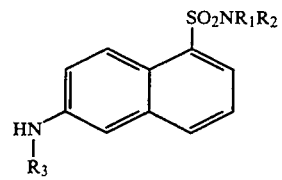

Chem. Abstracts, 51: 4722a [Swiss patent No. 312,090] discloses the use of 2-amino-5-naphthalenesulfonic acid methylamide in the preparation of cobalt containing azo dyes.

Lawson and Mann, (J. Biol. Chem., 266: 11317–11327, 1991), which is incorporated herein by reference, describes the investigation of the activation of human coagulation factor IX by human tissue factor.-factor VIIa.PCPS.$Ca^{2+}$ and factor Xa. PCPS.$Ca^{2+}$ enzyme complexes. It is suggested that factors IX and X, when presented to the tissue factor.factor VIIa.PCPS.$Ca^{2+}$ complex, are both rapidly activated and that factor Xa, which is generated in the initial stages of the extrinsic pathway, participates in the first proteolytic step in the activation of factor IX, the generation of factor IXa.

Lawson et al., (J. Biol. Chem. 267: 4834–4843, 1992), which is incorporated herein by reference, discusses the development of a fluorescent substrate (6-Mes-D-Leu-Gly-Arg)amino-1-(diethyl)napthalenesulfonamide) which can be used to directly measure the enzymatic activity of factor VIIa in the presence and absence of tissue factor and phospholipid.

Butenas et al., (Biochem. 31: 5399–5411, 1992) which is incorporated herein by reference, describes 6-amino-1-naphthalenesulfonamides and 6-peptidylamino-1-naphthalenesulfonamides useful in the detection of serine proteases involved in coagulation and fibrinolysis.

Butenas et al., (Chemistry, [Lithuanian Academy of Sciences] 182: 144–153, 1992) which is incorporated herein by reference describes the synthesis of 6-amino-1-naphthalenesulfonamides and suggests that these compounds may be used as detecting groups in peptide substrates for proteases.

A major weakness with many of the existing synthetic substrates is their low rate of enzymatic hydrolysis. Thus, large amounts of enzyme are normally required for the assay. While these prior art substrates provide increased sensitivity over substrates designed to exploit absorbance changes between substrate and product, they are plagued with other problems: overlap between the fluorescence spectral properties of the substrate and its hydrolysis products, lack of adequate solubility of substrate and fluorescent product in aqueous buffer, rapid rate of nonenzymatic substrate hydrolysis, and stability of the generated fluorescent product to both photo and chemical decomposition.

Thus, fluorogenic protease substrates are needed that have high specificity for the desired proteolytic enzyme, minimal overlap between the fluorescent spectral properties of the substrate and the hydrolysis products, reasonable solubility of the substrate and fluorescent products in aqueous buffer, low rates of non-enzymatic hydrolysis, and stability of the generated fluorescent product to both photo and chemical lysis.

SUMMARY OF THE INVENTION

The present invention provides compounds of formula and the pharmaceutically acceptable salts thereof; wherein $R_1$ is hydrogen, straight or branched chain lower alkyl having 1–6 carbon atoms, straight or branched chain alkenyl having 2–8 carbon atoms, straight or branched chain alkynyl having 2–8 carbon atoms, cycloalkyl having 3–7 carbon atoms, alkylcycloalkyl where the alkyl portion has 1–6 carbon atoms, cycloalkylalkyl where the alkyl portion has 1–6 carbon atoms, or phenylalkyl where the alkyl portion is straight or branched chain alkyl having 1–6 carbon atoms, or a group of the formula

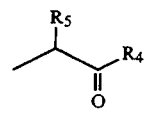

wherein $R_5$ represents an amino acid side chain and $R_4$ is hydroxy, an amino acid or a peptide residue;

$R_2$ is hydrogen, straight or branched chain lower alkyl having 1–6 carbon atoms, straight or branched chain alkenyl having 2–8 carbon atoms, straight or branched chain alkynyl having 2–8 carbon atoms, cycloalkyl having 3–7 carbon atoms, alkylcycloalkyl where the alkyl portion has 1–6 carbon atoms, cycloalkylalkyl where the alkyl portion has 1–6 carbon atoms, or phenylalkyl where the alkyl portion is straight or branched chain alkyl having 1–6 carbon atoms, or a group of the formula

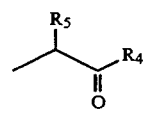

wherein $R_5$ represents an amino acid side chain and $R_4$ is hydroxy, an amino acid or a peptide residue; or $NR_1R_2$ forms a nitrogen heterocycle; and $R_3$ is an amino acid or a peptide residue.

The invention also provides methods for determining proteolytic enzyme activity comprising the steps of:

(a) contacting the enzyme with a substrate compound of formula I; and (b) measuring fluorescence intensity changes as a result substrate compound hydrolysis.

These compounds are highly selective substrates for proteolytic enzymes. By substrate is meant a compound of formula I where $R_3$ is an amino acid or a peptide residue. These compounds may be employed as substrates in assays for determining proteolytic enzyme activity or as inhibitors of the enzymes.

The invention provides proteolytic enzyme substrates having high specificity for the desired proteolytic enzyme.

The invention provides proteolytic enzyme substrates having minimal overlap between the fluorescent spectral properties of substrate and the hydrolysis products.

The invention provides proteolytic enzyme substrates having reasonable solubility of the substrate and fluorescent products in aqueous buffer.

The invention further provides proteolytic enzyme substrates that have low rates of non-enzymatic hydrolysis of substrates.

The invention provides proteolytic enzyme substrates having high stability of the generated fluorescent product to both photo and chemical lysis.

The invention also provides proteolytic enzyme inhibitors of formula I.

The invention further provides compounds of formula I where $R_3$ is hydrogen which are fluorescent products stable to both photo and chemical lysis. These fluorescent products are generated by a reaction between a 6-peptidylamino-1-naphthalenesulfonamide substrate and a proteolytic enzyme. These compounds where $R_3$ is hydrogen are also useful as starting materials for preparing the 6-peptidylamino-1-naphthalenesulfonamide substrates.

DETAILED DESCRIPTION OF THE INVENTION

Figure 1:
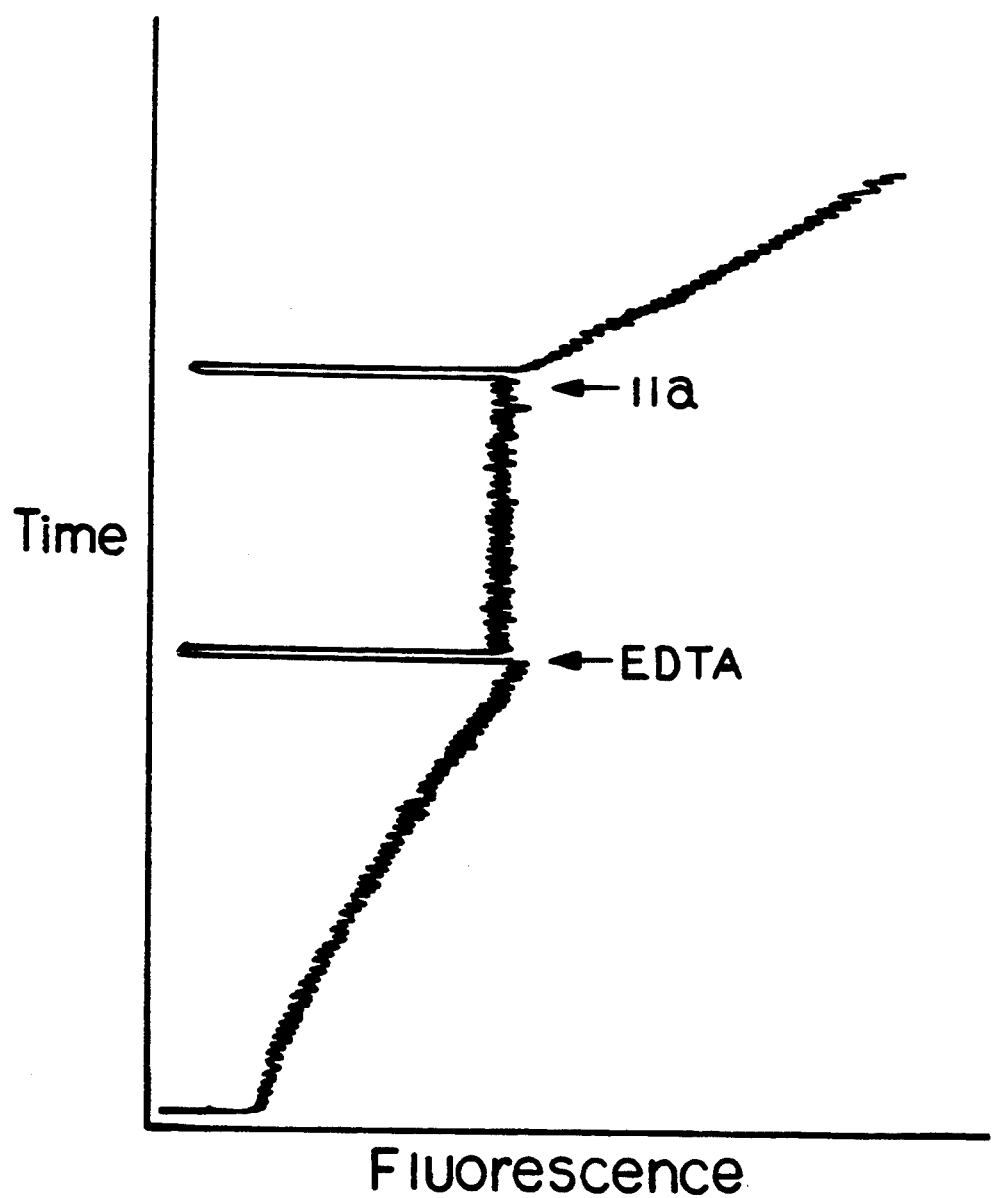
FIG. 1 is a direct tracing of factor VIIa substrate [6-(Mes-D-Leu-Gly-Arg)amino-1-(diethyl)naphthalenesulfonamide]hydrolysis in the presence of tissue factor. Substrate hydrolysis was followed by the addition of EDTA, and thrombin (IIa) to the reaction mixture.

The present invention provides compounds of formula

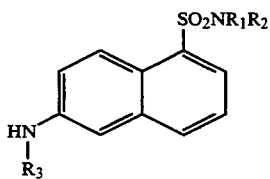

and the pharmaceutically acceptable non-toxic salts thereof; wherein $R_1$ is hydrogen, straight or branched chain lower alkyl having 1-6 carbon atoms, straight or branched chain alkenyl having 2-8 carbon atoms, straight or branched chain alkynyl having 2-8 carbon atoms, cycloalkyl having 3-7 carbon atoms, alkylcycloalkyl where the alkyl portion has 1-6 carbon atoms, cycloalkylalkyl where the alkyl portion has 1-6 carbon atoms, or phenylalkyl where the alkyl portion is straight or branched chain alkyl having 1-6 carbon atoms, or a group of the formula

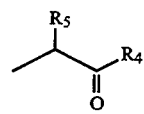

wherein $R_5$ represents an amino acid side chain and $R_4$ is hydroxy, an amino acid or a peptide residue;

$R_2$ is hydrogen, straight or branched chain lower alkyl having 1-6 carbon atoms, straight or branched chain alkenyl having 2-8 carbon atoms, straight or branched chain alkynyl having 2-8 carbon atoms, cycloalkyl having 3-7 carbon atoms, alkylcycloalkyl where the alkyl portion has 1-6 carbon atoms, cycloalkylalkyl where the alkyl portion has 1-6 carbon atoms, or phenylalkyl where the alkyl portion is straight or branched chain alkyl having 1-6 carbon atoms, or a group of the formula

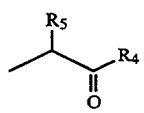

wherein $R_5$ represents an amino acid side chain and $R_4$ is hydroxy, an amino acid or a peptide residue; or $NR_1R_2$ forms a nitrogen heterocycle; and $R_3$ is an amino acid or a peptide residue.

The invention also provides compounds of formula II:

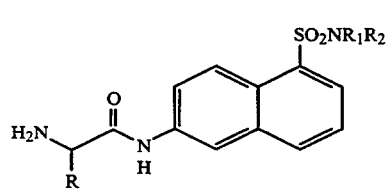

and the pharmaceutically acceptable non-toxic salts thereof; wherein $R_1$ is hydrogen, straight or branched chain lower alkyl having 1-6 carbon atoms, straight or branched chain alkenyl having 2-8 carbon atoms, straight or branched chain alkynyl having 2-8 carbon atoms, cycloalkyl having 3-7 carbon atoms, alkylcycloalkyl where the alkyl portion has 1-6 carbon atoms, cycloalkylalkyl where the alkyl portion has 1-6 carbon atoms, or phenylalkyl where the alkyl portion is straight or branched chain alkyl having 1-6 carbon atoms, or a group of the formula

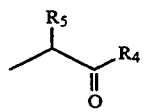

wherein R5 represents an amino acid side chain and R4 is hydroxy, an amino acid or a peptide residue;

R2 is hydrogen, straight or branched chain lower alkyl having 1-6 carbon atoms, straight or branched chain alkenyl having 2-8 carbon atoms, straight or branched chain alkynyl having 2-8 carbon atoms, cycloalkyl having 3-7 carbon atoms, alkylcycloalkyl where the alkyl portion has 1-6 carbon atoms, cycloalkylalkyl where the alkyl portion has 1-6 carbon atoms, or phenylalkyl where the alkyl portion is straight or branched chain alkyl having 1-6 carbon atoms, or a group of the formula

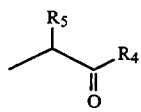

wherein R5 represents an amino acid side chain and R4 is hydroxy, an amino acid or a peptide residue; or NR1R2 forms a nitrogen heterocycle; and R represents —CH2CH2CH2CH2NH2 or —CH2CH2CH2NH—C(NH)—NH2.

The invention further provides compounds of formula I where R3 is hydrogen, i.e., 6-amino-1-naphthalenesulfonamides.

Representative compounds of the present invention, which are encompassed by formula I, include their non-toxic pharmaceutically acceptable salts.

Non-toxic pharmaceutically acceptable salts include salts of acids such as, for example, hydrochloric, phosphoric, hydrobromic, sulfuric, sulfinic, formic, toluene sulfonic, hydroiodic, acetic, trifluoroacetic and the like. Those skilled in the art will recognize a wide variety of non-toxic pharmaceutically acceptable addition salts.

Each of these substrates comprises an amino acid or peptide residue coupled to a detecting group. By detecting group is meant a chemical group or moiety capable of being both coupled to another molecule and detected by various chemical or spectroscopic methods. The specific detecting groups of the invention are 6-amino-1-naphthalenesulfonamides. The 6-amino-1-naphthalenesulfonamide detecting groups may be represented by formula I where R3 is hydrogen. The 6-amino-1-naphthalenesulfonamide detecting groups are liberated as products of a reaction between a 6-peptidylamino-1-naphthalenesulfonamide substrate and a proteolytic enzyme.

By peptide residue is meant a group comprising at least two amino acids coupled, for example, by an α peptide bond. The peptide residues of the invention may be obtained by proteolytic processing of an existing natural product, chemical synthesis from blocked amino acids or by molecular biological approaches using cells in vitro. An amino acid, or the amino acids used in the preparation of the peptide residues, may be either naturally or non-naturally occurring amino acids. The peptide residues may optionally contain various amino or carboxy protecting groups.

By lower alkyl in the present invention is meant straight or branched chain alkyl groups having 1-6 carbon atoms, such as, for example, methyl, ethyl, propyl, isopropyl, n-butyl, isobutyl, tert-butyl, pentyl, 2-pentyl, isopentyl, neopentyl, hexyl, 2-hexyl, 3-hexyl, and 3-methylpentyl.

By cycloalkyl is meant radicals of the formula

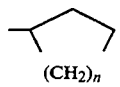

where n is 0 or an integer from 1-4.

By alkylcycloalkyl is meant radicals of the formula

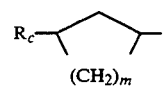

where the $R_c$ is a lower alkyl and m is 0 or an integer from 1-4.

By cycloalkylalkyl is meant radicals of the formula

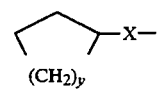

where X forms an straight or branched chain alkenylene group having 1-6 carbon atoms and y is 0 or an integer from 1-4.

By alkenyl as used herein is meant a straight or branched acyclic hydrocarbon having at least one double bond and having 2-8 carbon atoms.

By alkynyl is meant a straight or branched acyclic hydrocarbon having at least one triple bond and having 2-8 carbon atoms.

By nitrogen heterocycle in the invention is meant any cyclic carbon containing group that includes at least one nitrogen atom. Such a group may also include other atoms such as oxygen and sulfur.

By amino acid side chain is meant a substituent on the carbon alpha to the amino acid carboxy group.

These compounds are highly selective substrates for proteolytic enzymes. As is shown below in Table A, the 6-amino-1-naphthalenesulfonamide (ANSN) detecting groups of the invention confer additional specificity to the overall kinetic efficiency of substrate hydrolysis when compared to the p-nitroanilide substrate chromozyme TH (American Diagnostics).

Thus, these compounds may be employed as substrates in assays for determining proteolytic enzymes or as inhibitors of the enzymes. The substrates of the invention can be used to detect proteolytic enzymes such as catalytically active serine proteases involved in blood coagulation and thrombolysis. Examples of such serine proteases are tissue plasminogen activator, urokinase, factor VIIa, factor IIa, factor IXa, factor Xa, plasmin, and activated protein C.

The substrates are conveniently synthesized in relatively high yields using any of a variety of synthetic methodologies. An exemplary synthetic scheme is set forth below in Schemes I–III.

Each of the 6-amino-1-naphthalenesulfonamide detecting groups, i.e., the free fluorophores, have excitation maxima near 350 nm with emission maxima ranging from 465 to 476 nm. Fluorescent measurements show a 2.2 fold range in the intensities of the fluorescent signals among the fifteen synthesized compounds. The 6-peptidylamino-1-naphthalenesulfonamide fluorogenic substrates have a relative fluorescent intensity at 470 nm which is less than 0.1% of that of the respective free fluorophore. Detection of the free fluorophore can be reliably achieved (>2× background) at a concentration of about $10^{-9}$M in the presence of about $10^{-6}$ fluorogenic substrate. Continuous excitation of any ANSN at 352 nm for a period of 30 minutes resulted in no significant (<2%) deterioration of the fluorescence signal.

The 6-amino-1-naphthalenesulfonamide detecting group increased the specificity of the overall kinetic efficiency of substrate hydrolysis by thrombin relative to the rate of hydrolysis of the p-nitroanilide substrate chromozyme TH (American Diagnostics). Commercially available substrate (Chromozyme TH, TosGPR-p-NA) was compared to a substrate of the present invention, Tosgly-pro-arg-ANSN(i-C$_4$H$_9$) (TosGPR-ANSNH(i-C$_4$H$_9$)) in an assay performed at 22° C. in 0.02M TBS buffer at pH 7.4, containing 0.15M NaCl. The data are shown below in Table A.

TABLE A

| Substrate | Kinetic Constants | Enzyme IIa | Xa |
|---|---|---|---|
| Chromozyme TH | $K_m$ (μM) | 13.8 | 364 |
| | $K_{cat}$ | 14.1 | 244 |
| | $K_{cat}/K_m$ | $1.02 \times 10^6$ | $0.67 \times 10^6$ |
| TosGPR-ANSNH(i-C$_4$H$_9$) | $K_m$ | 10.5 | 132 |
| | $K_{cat}$ | 45.6 | 11.2 |
| | $K_{cat}/K_m$ | $4.34 \times 10^6$ | $0.08 \times 10^6$ |

The ANSN detecting group clearly conferred added specificity to the substrate for factor IIa, while decreasing substrate reactivity with factor Xa. The result of incorporating the ANSN detecting group of the invention increased the factor IIa specificity of this tripeptide about 51-fold, with respect to factor Xa, relative to the p-nitroanilide detecting group.

When coupled to methanesulfonyl-D-leucinyl-glycinyl-arginine(Mes-D-Leu-Gly-Arg), 6-amino-1-(N,N-diethyl)napthalenesulfonamide the resulting substrate yielded significant reactivity with factor VIIa. This substrate was sufficiently reactive with factor VIIa to allow reliable quantitation of factor VIIa activity at concentrations of about $10^{-9}$M. Further, this substrate was useful for the measurement of factor VIIa activity when it was bound to its co-factor protein tissue factor. The interaction of tissue factor with factor VIIa enhanced the factor VIIa dependent substrate hydrolysis by 120 fold. Thus, the invention provides unique substrates suitable for measuring both the activity of factor VIIa directly and in complex reactions involving the interaction between tissue factor and factor VIIa.

In addition, the compounds of the invention can be used as inhibitors of various proteases. Such compounds will minimally act as competitive inhibitors to reduce the rate of reaction of the protease with its natural substrate and can thus act to reduce natural proteolytic activity of enzymes either in vivo or in vitro.

These compounds are particularly useful as substrates for enzymes involved in the blood clotting process, notably factor IXa, factor VIIa, factor Xa, thrombin, and activated protein C, especially factors IXa and VIIa. Compounds in which hydrolysis of the aminoacyl bond is slow (relative to that of other compounds in the series) are particularly useful as inhibitors. Whether a given compound of the invention will be more useful as a substrate or as an inhibitor of the enzyme can readily be determined by measurement of binding affinities and hydrolysis rates, as described elsewhere in this application. Also see, for example, Alan Fersht, *Enzyme Structure and Mechanism*, W. H. Freeman and Company, New York, 1985, which is herein incorporated by reference, for a discussion of techniques by which these binding and reaction parameters can be measured. All of these aspects of the invention can be practiced by administration of the compound to any patient who would benefit by a reduction of clotting rates because of the interaction described above. The compounds are particularly useful in treatment of any disease or disorder that would be ameliorated by inhibition of the action of thrombin with existing medications, including both platelet driven (arterial) and thrombin driven (veneous) clotting processes, such as the treatment of deep vein thrombosis, myocardial infarction, and stroke.

When used in vitro, the compositions are used in the same manner and in place of other currently available anti-coagulants.

The compounds of formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of formula I and a pharmaceutically acceptable carrier. One or more compounds of formula I may be present in association with one or more non-toxic pharmaceutically acceptable carriers and/or diluents and/or adjuvants and if desired other active ingredients. The pharmaceutical compositions containing compounds of formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions more may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of formula I may be administered parenterally in a sterile medium. The drug, depending on the vehicle and concentration used, can either be suspended or dissolved in the vehicle. Advantageously, adjuvants such as a local anaesthetic, preservative and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration and rate of excretion.

An illustration of the synthesis of the compounds of the present invention is shown in Schemes I–III. Those having skill in the art will recognize that the starting materials may be varied and additional steps employed to produce compounds encompassed by the present invention, as demonstrated by the following examples.

Scheme I

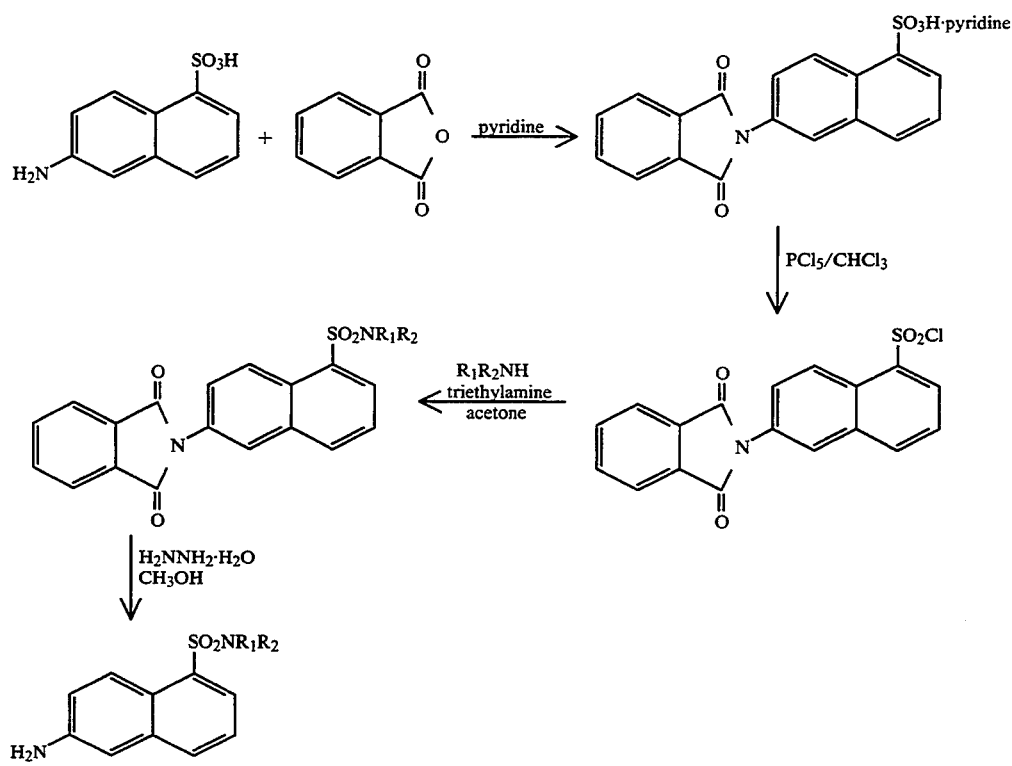

Scheme II

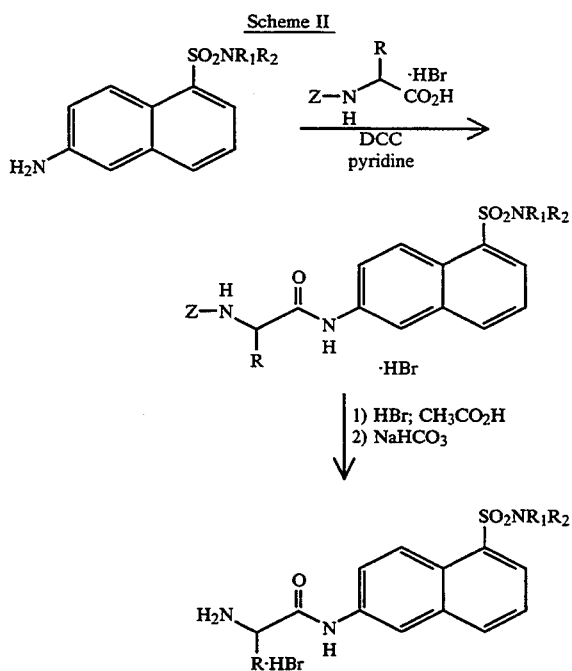

Scheme III

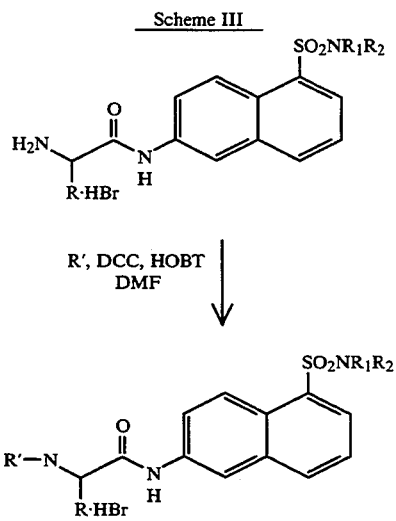

In each of the above schemes:

$R_1$ is hydrogen, straight or branched chain lower alkyl having 1-6 carbon atoms, straight or branched chain alkenyl having 2-8 carbon atoms, straight or branched chain alkynyl having 2-8 carbon atoms, cycloalkyl having 3-7 carbon atoms, alkylcycloalkyl where the alkyl portion has 1-6 carbon atoms, cycloalkylalkyl where the alkyl portion has 1-6 carbon atoms, or phenylalkyl where the alkyl portion is straight or branched chain alkyl having 1-6 carbon atoms, or a group of the formula

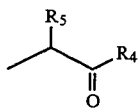

wherein R₅ represents an amino acid side chain and R₄ is hydroxy, an amino acid or a peptide residue;

R₂ is hydrogen, straight or branched chain lower alkyl having 1-6 carbon atoms, straight or branched chain alkenyl having 2-8 carbon atoms, straight or branched chain alkynyl having 2-8 carbon atoms, cycloalkyl having 3-7 carbon atoms, alkylcycloalkyl where the alkyl portion has 1-6 carbon atoms, cycloalkylalkyl where the alkyl portion has 1-6 carbon atoms, or phenylalkyl where the alkyl portion is straight or branched chain alkyl having 1-6 carbon atoms, or a group of the formula

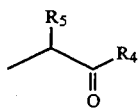

wherein R₅ represents an amino acid side chain and R₄ is hydroxy, an amino acid or a peptide residue; or NR₁R₂ forms a heterocycle having 3-5 carbon atoms; and R is —CH₂CH₂CH₂CH₂NH₂ or —CH₂CH₂CH₂N-H—C(NH)—NH₂, where the γ or ε NH₂ may be protected or unprotected; and R' is an amino acid or peptide residue.

The invention is illustrated further by the following examples which are not to be construed as limiting the invention in scope or spirit to the specific compounds or procedures described in them.

EXAMPLE 1

PREPARATION OF 6-AMINO-1-NAPHTHALENESULFONAMIDES 1. 6-phthalimido-1-naphthalenesulfonic acid pyridinium salt

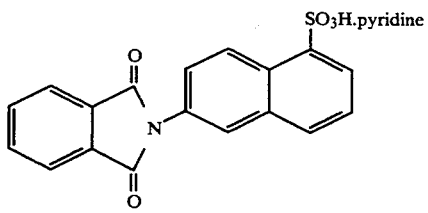

223 g (1 mol) of 6-amino-1-naphthalenesulfonic acid and 148 g (1 mol) of phthalic anhydride are boiled for 0.5 h in 1 liter of pyridine. After boiling, the reaction mixture is left at room temperature for 16 h. The precipitated product is filtered and washed with pyridine and water, and then recrystallized from boiling water. Yield 298 g (69%); mp 234°-237° C.; Anal. Calcd. for $C_{23}H_{16}N_2SO_5$:C 63.88, H 3.73, N 6.48, S 7.42; Found:C 63.74, H 3.81, N 6.52, S 6.99. When the 6-phthalimido-1-naphthalenesulfonic acid pyridinium salt was synthesized starting from 6-amino-1-naphthalenesulfonic acid sodium salt or triethylammonium salt, the calculated yields were 63% and 58% respectively.

2. 6-phthalimido-1-naphthalenesulfonyl chloride

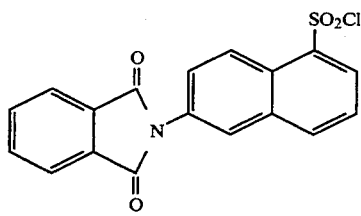

43.2 g (0.1 mol) of 6-phthalimido-1-naphthalenesulfonic acid pyridinium salt and 62.5 g (0.3 mol) of phosphorus pentachloride are boiled for 5 h in 600 ml of chloroform. Solvent and the POCl₃ formed in the reaction are evaporated under vacuum. The remaining product is then added to 2 liter of ice water. After 1 h the precipitated product is filtered, washed with water, dried, and recrystallized from toluene. Yield 36.8 g (99%); mp 248°-251° C.; Anal. Calcd. for $C_{18}H_{10}NSClO_4$:C 58.15, H 2.71, N 3.77, S 8.63, Cl 9.53; Found:C 58.02, H 2.84, N 3.73, S 9.01, Cl 9.32.

3. 6-phthalimido-1-(N,N-diethyl)naphthalenesulfonamide

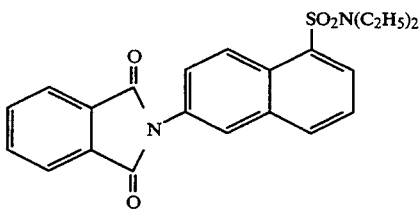

37.2 g (0.1 mol) 6-Phthalimido-1-naphthalenesulfonyl chloride were added to a solution of 10.3 ml (0.1 mol) diethylamine and 13.9 ml (0.1 mol) of triethylamine in 500 ml of acetone over 5 min. The reaction mixture was stirred at 20° C. for 4 h. The acetone was evaporated and the residue added to 1 liter of water. The precipitate was filtered, washed with water, dried, and recrystallized from methanol. Yield 34.3 g (84%); mp 199°-203° C.; Anal. Calcd. for $C_{24}H_{22}N_2SO_4$:C 64.69, H 4.94, N 6.86, S 7.84; Found:C 64.63, H 4.98, N 6.72, S 8.14.

Other 6-Phthalimido-1-naphthalenesulfonamides were prepared essentially according to the procedures set forth in parts 1-3 of Example 1. Data for these compounds is set forth below in Table 1.

TABLE 1

| 6-Phthalimido-1-Naphthalenesulfonamides | | | | | | | | |
|---|---|---|---|---|---|---|---|---|
| | | | | Analytical Data (Found/Calc.) | | | | |
| R¹ | R² | Yield % | Mp °C. | C | H | N | S | Formula |
| H | CH₃ | 88 | 186–189 | 62.37 | 3.91 | 7.78 | 8.48 | $C_{19}H_{14}N_2SO_4$ |
| H | C₂H₅ | 81 | 207–211 | 62.29 / 62.33 | 3.85 / 4.28 | 7.64 / 7.47 | 8.75 / 8.23 | $C_{20}H_{16}N_2SO_4$ |
| H | C₃H₇ | 91 | 176–179 | 63.15 / 63.82 | 4.24 / 4.75 | 7.36 / 7.28 | 8.43 / 8.09 | $C_{21}H_{18}N_2SO_4$ |

TABLE 1-continued

6-Phthalimido-1-Naphthalenesulfonamides

| R¹ | R² | Yield % | Mp °C. | C | H | N | S | Formula |
|---|---|---|---|---|---|---|---|---|
| | | | | \[Analytical Data (Found/Calc.)\] | | | | |
| H | i-$C_3H_7$ | 72 | 201–203 | 63.95 / 62.12 | 4.60 / 4.55 | 7.10 / 7.05 | 8.12 / 8.04 | $C_{21}H_{18}N_2SO_4$ |
| H | $C_4H_9$ | 59 | 201–205 | 63.95 / 64.88 | 4.60 / 4.87 | 7.10 / 6.72 | 8.12 / 7.61 | $C_{22}H_{20}N_2SO_4$ |
| H | i-$C_4H_9$ | 79 | 150–153 | 64.69 / 64.71 | 4.94 / 4.85 | 6.86 / 6.98 | 7.85 / 7.25 | $C_{22}H_{20}N_2SO_4$ |
| H | $C_5H_{11}$ | 96 | 168–172 | 64.69 / 65.60 | 4.94 / 5.28 | 6.86 / 6.71 | 7.85 / 7.18 | $C_{23}H_{22}N_2SO_4$ |
| H | cyclo-$C_6H_{11}$ | 92 | 206–209 | 65.39 / 66.48 | 5.25 / 5.07 | 6.63 / 6.32 | 7.59 / 7.14 | $C_{24}H_{22}N_2SO_4$ |
| H | benzyl | 89 | 243–247 | 9.3–4 / 67.69 | 5.10 / 4.09 | 6.45 / 6.16 | 7.38 / 7.26 | $C_{25}H_{18}N_2SO_4$ |
| $CH_3$ | $CH_3$ | 90 | 152–155 | 67.86 / 63.14 | 4.10 / 4.35 | 6.33 / 7.53 | 7.25 / 8.40 | $C_{20}H_{16}N_2SO_4$ |
| $C_2H_5$ | $C_2H_5$ | 84 | 199–203 | 63.15 / 64.63 | 4.24 / 4.98 | 7.36 / 6.72 | 8.43 / 8.14 | $C_{22}H_{20}N_2SO_4$ |
| | | | | 64.69 | 4.94 | 6.86 | 7.84 | |

4. 6-amino-1-(N,N-diethyl)naphthalenesulfonamide

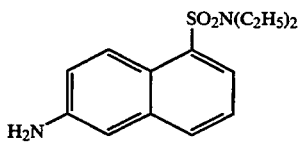

40.8 g (0.1 mol) of 6-phthalimido-1-(N,N-diethyl)-naphthalenesulfonamide was refluxed for 4.5 h in 500 ml of methanol containing 4.9 ml (0.1 mol) of hydrazine monohydrate. The methanol was evaporated and the residue extracted twice with 200 ml of boiling chloroform. The chloroform was evaporated and the product recrystallized from methanol. Yield 12.8 g (46%); mp 106°–108° C.; Anal. Calcd. for $C_{14}H_{18}N_2SO_2$:C 60.41, H 6.52, N 10.06, S 11.52; Found:C 60.54, H 6.57, N 9.89, S 11.35.

Other 6-amino-1-naphthalenesulfonamides were prepared essentially according to the procedures set forth in part 4 of Example 1. Data for these compounds is set forth below in Table 2.

TABLE 2

6-Amino-1-Naphthalenesulfonamides ANSNR₁R₂

| R¹ | R² | Yield % | Mp °C. | R_f^b | C | H | N | S | Formula | MW | Emission Maxima (nm) | Relative Fluorescence^a |
|---|---|---|---|---|---|---|---|---|---|---|---|---|
| H | $CH_3$ | 57 | 145–148 | 0.38 | 56.10 / 55.91 | 5.16 / 5.12 | 11.96 / 11.85 | 13.11 / 13.57 | $C_{11}H_{12}N_2SO_2$ | 236.29 | 468 | 92 |
| H | $C_2H_5$ | 83 | 109–113 | 0.55 | 57.72 / 57.58 | 5.72 / 5.64 | 11.40 / 11.19 | 12.57 / 12.81 | $C_{12}H_{14}N_2SO_2$ | 250.31 | 466 | 78 |
| H | $C_3H_7$ | 48 | — | 0.61 | 59.26 / 59.07 | 6.27 / 6.10 | 10.73 / 10.60 | 11.70 / 12.13 | $C_{13}H_{16}N_2SO_2$ | 264.34 | 470 | 93 |
| H | i-$C_3H_7$ | 78 | 140–144 | 0.51 | 58.88 / 59.07 | 6.09 / 6.10 | 10.58 / 10.60 | 12.04 / 12.13 | $C_{13}H_{16}N_2SO_2$ | 264.34 | 468 | 76 |
| H | $C_4H_9$ | 46 | 76–79 | 0.48 | 60.56 / 60.41 | 6.45 / 6.52 | 10.20 / 10.06 | 11.37 / 11.52 | $C_{14}H_{18}N_2SO_2$ | 278.37 | 467 | 63 |
| H | i-$C_4H_9$ | 79 | 48–50 | 0.57 | 60.40 / 60.41 | 6.62 / 6.52 | 9.93 / 10.06 | 11.02 / 11.52 | $C_{14}H_{18}N_2SO_2$ | 278.37 | 468 | 100 |
| H | t-$C_4H_9$ | 69 | 198–200 | 0.55 | 60.47 / 60.41 | 6.56 / 6.52 | 10.14 / 10.06 | 11.26 / 11.52 | $C_{14}H_{18}N_2SO_2$ | 278.37 | 465 | 112 |
| H | $C_5H_{11}$ | 66 | 87–90 | 0.62 | 61.72 / 61.62 | 6.86 / 6.89 | 9.40 / 9.58 | 10.92 / 10.96 | $C_{15}H_{20}N_2SO_2$ | 292.40 | 469 | 90 |
| H | cyclo-$C_6H_{11}$ | 48 | 136–140 | 0.69 | 63.15 / 63.13 | 6.81 / 6.62 | 9.18 / 9.20 | 10.84 / 10.53 | $C_{16}H_{20}N_2SO_2$ | 304.41 | 466 | 101 |
| H | benzyl | 64 | 148–150 | 0.67 | 65.52 / 65.36 | 5.19 / 5.16 | 8.82 / 8.97 | 9.21 / 10.26 | $C_{17}H_{16}N_2SO_2$ | 312.39 | 467 | 75 |
| $CH_3$ | $CH_3$ | 81 | 92–94 | 0.63 | 57.56 / 57.58 | 5.66 / 5.64 | 11.30 / 11.19 | 12.00 / 12.81 | $C_{12}H_{14}N_2SO_2$ | 250.31 | 472 | 65 |
| $C_2H_5$ | $C_2H_5$ | 46 | 106–108 | 0.74 | 60.54 / 60.41 | 6.57 / 6.52 | 9.89 / 10.06 | 11.35 / 11.52 | $C_{14}H_{18}N_2SO_2$ | 278.37 | 470 | 89 |
| | $(CH_2)_5$ | 71 | 140–143 | 0.78 | 62.16 / 62.04 | 6.21 / 6.25 | 9.57 / 9.65 | 10.81 / 11.04 | $C_{15}H_{18}N_2SO_2$ | 290.38 | 473 | 68 |
| | $(CH_2)_6$ | 44 | 187–190 | 0.79 | 63.28 / 63.13 | 4.46 / 6.62 | 9.07 / 9.20 | 10.18 / 10.53 | $C_{16}H_{20}N_2SO_2$ | 304.41 | 469 | 96 |
| | morpholyl | 74 | 80–83 | 0.63 | 57.34 | 5.67 | 9.72 | 10.74 | $C_{14}H_{16}N_2SO_3$ | 292.36 | 476 | 41 |

TABLE 2-continued

6-Amino-1-Naphthalenesulfonamides ANSNR₁R₂

| R¹ | R² | Yield % | Mp °C. | R_f[b] | Analytical Data (Found/Calc.) | | | | Formula | MW | Emission Maxima (nm) | Relative Fluorescence[a] |
|---|---|---|---|---|---|---|---|---|---|---|---|---|
| | | | | | C | H | N | S | | | | |
| | | | | | 57.51 | 5.52 | 9.58 | 10.97 | | | | |

[a]Measured in TBS, pH 7.4. 22°C.. Concentration of ANSN-R₁R₂ = 1 μM. Fluorescence is expressed relative of ANSNH-(i-C₄H₉). Excitation wavelength = 352 nm. Emission wavelength = 470 nm.
[b]Ethylacetate-chloroform 1:1

EXAMPLE 2

Preparation of 6-L-arginylamino-1-naphthalenesulfamide hydrobromides 1. 6-($N^\alpha$-benzyloxycarbonyl-L-arginyl)amino-1-(N,N-diethyl)napthalenesulfonamide hydrobromides

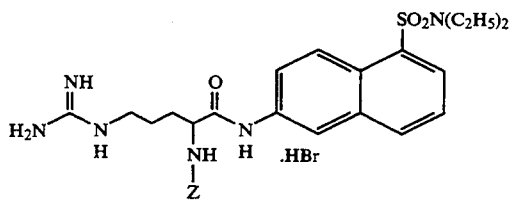

3.89 g (0.01 mol) N-benzyloxycarbonyl-L-arginine hydrobromide and 2.78 g (0.01 mol) 6-amino-1-(N,Ndiethyl)naphthalenesulfonamide were dissolved in 15 ml of dry pyridine after which 30 ml of dry toluene was added to the solution. The toluene was evaporated in a vacuum and the reaction mixture was cooled to −20° C. Next, 2.68 g (0.013 mol) of 1,3-dicyclohexylcarbodiimide (DCC) in 6 ml of dry pyridine was added to the reaction mixture. The mixture was maintained at −20° C. for 30 minutes and then warmed to 4° C. for 1 h, and subsequently mixed by stirring at 20° C. for 20 h. The precipitated dicyclohexylurea was filtered, the pyridine was removed under vacuum and the remaining oil was dissolved in 40 ml n-propanol-cholorform (1:3). The resulting solution was washed by the as follows: 1× with 15 ml of water, 1× with 15 ml of saturated sodium chloride containing 1 ml of concentrated HCl, 1× with 15 ml of 2% ammonia in water, and 1× with 15 ml of water. The organic layer was dried over anhydrous $Na_2SO_4$, the solvents were evaporated, and the residual oil was hardened by grinding under dry toluene. The reaction product was then filtered, washed with dry toluene and dry ether, and recrystallized from 1-propanol. Yield 5.64 g (84%); mp 104°–112° C.; $R_f$=0.72 (butanol:acetic acid:$H_2O$, BAW, 4:1:2); $[\alpha]_D^{20}$= −12.8° (C 1; methanol); Anal. Calcd. for $C_{28}H_{37}N_6BrSO_5$:C 51.77, H 5.74, N 12.94, Br 12.30, S 4.94; Found:C 51.63, H 5.85, N 12.76, Br 11.88, S 4.58.

Other 6-($N^\alpha$-carbobenzyloxy-L-arginyl)amino-1-naphthalenesulfamide hydrobromides were prepared essentially according to the procedures set forth in part 1 of Example 2. Data for these compounds is set forth below in Table 3.

TABLE 3

($N^\alpha$—Z) ArgANSNR₁R₂.HBr

| R¹ | R² | Yield % | DMP °C. | $[\alpha]^{20}$ cl;CH₃OH | R_f BAW412 | C | H | N | S | Br | |
|---|---|---|---|---|---|---|---|---|---|---|---|
| H | CH₃ | 81 | 127–132 | −13.3° | 0.68 | 49.59 | 5.32 | 13.63 | 4.63 | 12.42 | C₂₅H₃₁N₆BrSO₅ |
| | | | | | | 49.42 | 5.14 | 13.83 | 5.28 | 13.15 | |
| H | C₂H₅ | 93 | 134–138 | −14.1° | 0.69 | 50.36 | 5.52 | 13.34 | 4.53 | 12.06 | C₂₆H₃₃N₆BrSO₅ |
| | | | | | | 50.24 | 5.35 | 13.52 | 5.10 | 12.86 | |
| H | C₃H₇ | 94 | 118–124 | −14.9° | 0.71 | 51.21 | 5.61 | 13.62 | 4.29 | 11.72 | C₂₇H₃₅N₆BrSO₅ |
| | | | | | | 51.02 | 5.55 | 13.22 | 6.04 | 12.57 | |
| H | i-C₃H₇ | 92 | 119–124 | −14.3° | 0.70 | 51.17 | 5.45 | 13.40 | 4.23 | 12.19 | C₂₇H₃₅N₆BrSO₅ |
| | | | | | | 51.02 | 5.55 | 13.22 | 5.04 | 12.57 | |
| H | C₄H₉ | 91 | 122–127 | −14.6° | 0.67 | 51.83 | 5.93 | 12.78 | 4.13 | 11.51 | C₂₈H₃₇N₆BrSO₅ |
| | | | | | | 51.77 | 5.74 | 12.94 | 4.94 | 12.30 | |
| H | i-C₄H₉ | 95 | 122–126 | −13.5° | 0.70 | 51.62 | 5.88 | 13.07 | 4.12 | 11.84 | C₂₈H₃₇N₆BrSO₅ |
| | | | | | | 51.77 | 5.74 | 12.94 | 4.94 | 12.30 | |
| H | t-C₄H₉ | 20 | 145–148 | −13.3° | 0.55 | 51.92 | 5.81 | 12.85 | 4.63 | 12.03 | C₂₈H₃₇N₆BrSO₅ |
| | | | | | | 51.77 | 5.74 | 12.94 | 4.94 | 12.30 | |
| H | C₅H₁₁ | 91 | 120–124 | −16.0° | 0.77 | 52.58 | 6.13 | 12.85 | 4.42 | 11.89 | C₂₉H₃₉N₆BrSO₅ |
| | | | | | | 52.49 | 5.92 | 12.66 | 4.94 | 12.04 | |
| H | cyclo-C₆H₁₁ | 94 | 135–141 | 012.6° | 0.69 | 53.21 | 5.96 | 12.63 | 4.32 | 11.48 | C₃₀H₃₉N₆BrSO₅ |
| | | | | | | 53.33 | 5.82 | 12.44 | 4.75 | 11.83 | |
| H | benzyl | 96 | 161–164 | −13.5° | 0.63 | 54.58 | 5.25 | 12.14 | 4.23 | 10.93 | C₃₁H₃₅N₆BrSO₅ |
| | | | | | | 54.46 | 5.16 | 12.29 | 4.69 | 11.69 | |
| CH₃ | CH₃ | 78 | 117–121 | −13.4° | 0.69 | 50.39 | 5.54 | 13.42 | 4.33 | 12.30 | C₂₆H₃₃N₆BrSO₅ |
| | | | | | | 50.24 | 5.35 | 13.52 | 5.16 | 12.85 | |
| C₂H₅ | C₂H₅ | 84 | 106–112 | −12.8° | 0.72 | 51.63 | 5.85 | 12.75 | 4.58 | 11.88 | C₂₈H₃₇N₆BrSO₅ |
| | | | | | | 51.77 | 5.74 | 12.94 | 4.94 | 12.30 | |
| | (CH₂)₅ | 89 | 118–123 | −12.8° | 0.71 | 52.49 | 5.81 | 12.62 | 4.53 | 11.87 | C₂₉H₃₇N₆BrSO₅ |
| | | | | | | 52.65 | 5.64 | 12,70 | 4.85 | 12.08 | |
| | (CH₂)₆ | 91 | 107–113 | −13.8° | 0.73 | 53.41 | 5.73 | 12.60 | 4.54 | 11.57 | C₃₀H₃₉N₆BrSO₅ |
| | | | | | | 53.33 | 5.82 | 12.44 | 4.75 | 11.83 | |
| | morpholyl | 84 | 119–125 | −12.3° | 0.69 | 50.71 | 5.18 | 12.51 | 4.71 | 11.79 | C₂₈H₃₅N₆BrSO₆ |

TABLE 3-continued (N<sup>α</sup>—Z) ArgANSNR<sub>1</sub>R<sub>2</sub>.HBr

| R¹ | R² | Yield % | $_D$MP °C. | $[\alpha]_D^{20}$ cl;CH$_3$OH | $R_f$ BAW412 | C | H | N | S | Br |
|---|---|---|---|---|---|---|---|---|---|---|
| | | | | | | 50.68 | 5.32 | 12.66 | 4.83 | 12.04 |

2. 6-L-arginylamino-1-(N,N-diethyl)naphthalenesulfonamide hydrobromide.

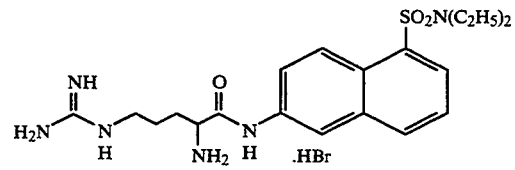

6.50 g (0.01 mol) of 6-(N<sup>α</sup>-benzyloxycarbonyl-L-arginyl)amino-1-(N,N-diethyl)naphthalenesulfonamide hydrobromide was dissolved in 10 ml of 3N HBr in glacial acetic acid and the solution was maintained at room temperature for 2 hours. The reaction mixture was then added to 100 ml of dry ether. After 10 minutes the precipitate was filtered, washed with ether, and dried. The dry 6-L-arginylamino-1-(N,N-diethyl)naphthalenesulfonamide dihydrobromide was dissolved in 10 ml of water. This solution was then poured into a separation funnel, and 50 ml of n-butanol is added. This is followed by the addition of 5% NaHCO$_3$ until the pH of the water layer was about 7.5. The organic layer was then washed with water and concentrated under vacuum until the final volume of the solution was between 3-5 ml. The product was precipitated with dry diethyl ether, filtered, washed with ether and dried. Yield 4 73 g (92%); R$_f$=0.44 (BAW 412); $[\alpha]_D^{20}$=−0.5° (C 1; DMSO); Anal. Calcd. for C$_{20}$H$_{31}$N$_6$BrSO$_3$:C 46.60, H 6.06, N 16.30, Br 15.50, S 6.22; Found:C 46.51, H 6.18, N 16.14, Br 15.12, S 6.56.

Other 6-L-arginylamino-1-naphthalenesulfonamide hydrobromides were prepared essentially according to the procedures set forth in part 2 of Example 2. Data for these compounds is set forth below in Table 4.

EXAMPLE 3

Preparation of Methanesulfonyl-D-Leucinyl-Glycine

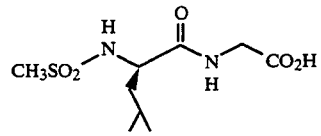

To 13.9 ml (0.1 mol) of triethylamine in 100 ml of dry chloroform at 0° C. was added 9.1 g (0.05 mol) of D-Leu-OCH$_3$.HCl. To this solution 4.5 ml (0.055 mol) of methanesulfonyl chloride was added at 0° C. while maintaining the reaction mixture above pH 8. After stirring at 20° C. for about 3 hours, the precipitated triethylamine hydrochloride was filtered and washed with chloroform. The filtrate was washed as follows: 1× with 50 ml 5% NaHCO$_3$, 1× with 50 ml 10% KHSO$_4$, 2× with 50 ml H$_2$O. The organic layer was dried over anhydrous MgSO$_4$, and the chloroform was evaporated under vacuum. The residual oil (Mes-D-Leu-OCH$_3$, 10 g, 0.0446 mol) was dissolved at 10° C. in 50 ml of dry methanol containing 1.5 g of sodium. To this solution was added 3 ml of H$_2$O and this reaction mixture was left for 72 hours at 20° C. The precipitate, Mes-D-Leu-ONa, was filtered, dried and dissolved in 50 ml of H$_2$O. The solution was acidified to pH 2 with concentrated HCl. The solution was then extracted with chloroform, and the organic layer was dried over anhydrous MgSO$_4$ and evaporated under vacuum. The residual oil (Mes-D-Leu-OH, 7.5 g, 0.0375 mol) was dissolved at 0° C. in 75 ml of chloroform containing 5.0 g (0.0375 mol) of Gly-OC$_2$H$_5$.HCl while maintaining the solution at pH 8 with triethylamine. To this solution at 0° C. was added 8.2 g (0.04 mol) of DCC in 15 ml of dry chloroform. This reaction mixture was held at 0° C. for 4 hours and then at 20° C. for 20 hours. The precipitated dicyclohexylurea was filtered and washed with CHCl$_3$. The filtrate was washed with 30 ml 5% NaHCO$_3$, 30 ml 10% KHSO$_4$ and 2×30 ml of H$_2$O, dried

TABLE 4

6-Arginylamino-1-naphthalenesulfonamide hydrobromides
ArgANSNR$_1$R$_2$.HBr

| R¹ | R² | Yield % | MP °C. | $[\alpha]_D^{20}$ cl;CH$_3$OH | $R_f$ BAW412 | Brutto formula |
|---|---|---|---|---|---|---|
| H | CH$_3$ | 85 | 98–104 | +3.3° | 0.40 | C$_{17}$H$_{25}$N$_6$BrSO$_3$ |
| H | C$_2$H$_5$ | 94 | 171–178 | −4.1° | 0.46 | C$_{18}$H$_{27}$N$_6$BrSO$_3$ |
| H | C$_3$H$_7$ | 95 | 133–138 | −2.1° | 0.41 | C$_{19}$H$_{29}$N$_6$BrSO$_3$ |
| H | i-C$_3$H$_7$ | 91 | 167–171 | −1.0° | 0.42 | C$_{19}$H$_{29}$N$_6$BrSO$_3$ |
| H | C$_4$H$_9$ | 90 | 128–133 | −2.0° | 0.47 | C$_{20}$H$_{31}$N$_6$BrSO$_3$ |
| H | i-C$_4$H$_9$ | 96 | 161–165 | −3.2° | 0.47 | C$_{20}$H$_{31}$N$_6$BrSO$_3$ |
| H | t-C$_4$H$_9$ | 85 | 163–168 | −1.5° | 0.33 | C$_{20}$H$_{31}$N$_6$BrSO$_3$ |
| H | C$_5$H$_{11}$ | 92 | 128–132 | −5.0° | 0.40 | C$_{21}$H$_{33}$N$_6$BrSO$_3$ |
| H | cyclo-C$_6$H$_{11}$ | 89 | 151–156 | −2.0° | 0.43 | C$_{22}$H$_{33}$N$_6$BrSO$_3$ |
| H | benzyl | 98 | 149–152 | −1.0° | 0.50 | C$_{23}$H$_{29}$N$_6$BrSO$_3$ |
| CH$_3$ | CH$_3$ | 83 | 99–102 | +4.3° | 0.41 | C$_{18}$H$_{27}$N$_6$BrSO$_3$ |
| C$_2$H$_5$ | C$_2$H$_5$ | 92 | 133–137 | −0.5° | 0.44 | C$_{20}$H$_{31}$N$_6$BrSO$_3$ |
| | (CH$_2$)$_5$ | 90 | 124–130 | −1.2° | 0.48 | C$_{21}$H$_{31}$N$_6$BrSO$_3$ |
| | (CH$_2$)$_6$ | 89 | 135–139 | −2.1° | 0.50 | C$_{22}$H$_{33}$N$_6$BrSO$_3$ |
| | morpholyl | 81 | 154–159 | +2.6° | 0.38 | C$_{20}$H$_{29}$N$_6$BrSO$_4$ | over anhydrous MgSO₄ and evaporated under vacuum. The residual oil (Mes-D-Leu-Gly-OC₂H₅, 8.4 g, 0.03 mol) was dissolved in 45 ml of methanol, and to the solution was added 20 ml of 2N NaOH. The solution was held at 20° C. for 24 hours and then diluted with water to a volume of 100 ml. This solution was concentrated under vacuum to a volume of 35 ml; this mixture was washed with 15 ml of chloroform and neutralized with concentrated HCl to pH 3. The mixture was washed with 15 ml of chloroform and the water was evaporated under vacuum. The residue was dissolved in 50 ml of acetone, the precipitated NaCl was removed by filtration, and the acetone was evaporated under vacuum. Yield 47.4%; mp 122°-126° C.; $[\alpha]_D^{20}$=+4.0 (C 1; CH₃OH); Anal. Calcd. for C₉H₁₈N₂SO₅:C 40.59, H 6.81, N 10.52, S 12.04; Found:C 40.47, H 6.93, N 10.28, S 12.32.

Other peptides were prepared according to Anderson, G. W., Zimmerman, J. E., & Callahan, F. H. (1964) *J. Am. Chem. Soc.* 86: 1839–1842.

EXAMPLE 4

Preparation of 6-(Mes-D-Leu-Gly-Arg)amino-1-(N,N-diethyl)napthalenesulfonamide

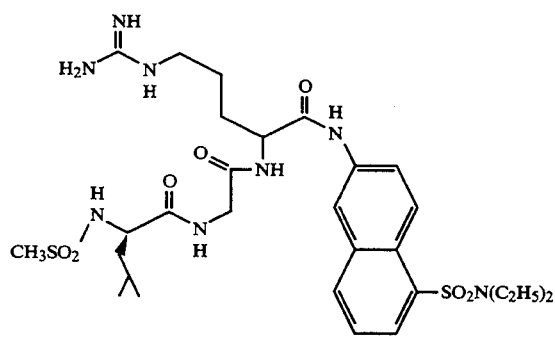

2.66 g (0.01 mol) of Mes-D-Leu-Gly.OH, 2.68 g (0.013 mol) of DCC and 1.35 g (0.01 mol) 1-hydroxybenzotriazole hydrate were added to 25 ml of dry DMF (cooled to −20° C.). The reaction mixture was maintained at 0° C. for 1 hour at which time 5.15 g (0.01 mol) of 6-L-arginylamino-1-(N,N-diethyl)naphthalenesulfonamide hydrobromide in 15 ml of DMF was added. The reaction mixture was stirred at 0° C. for 1 hour and then at 20° C. for 20 hours. The precipitated dicyclohexylurea was filtered and the filtrate was added to 150 ml of water. This solution was extracted with n-butanolethylacetate (1:1, 5×20 ml), the organic layer was washed with 5% NaHCO₃ (3×7 ml), 10% KHSO₄ (3×7 ml), and water (3×7 ml). The organic layer was concentrated to a final volume of 3–5 ml, the product was precipitated with dry ether, filtered, and subsequently washed with ether and dried. Yield 5.94 g (87%); mp 190°–205° C.; R$_f$=0.62 (BAW 412); $[\alpha]_D^{20}$= −12.9° (C 1; DMSO).

Other 6-peptidylamino-1-napththalenesulfonamides were prepared essentially according to the procedures set forth in Example 4. Data for these compounds is set forth below in Table 5.

TABLE 5

| Substrates | 6-Peptidylamino-1-Naphthalenesulfonamides | | | |
|---|---|---|---|---|
| | MW | % Yield | R$_f^a$ | $[\alpha]_D^{20b}$ |
| BocPFR-ANSNHC₃H₇ | 764.94 | 96 | 0.72 | −12.8 |
| PFR-ANSNHC₃H₇.2HCl | 737.74 | 82 | 0.28 | −6.8 |
| BoPFR-ANSNHC₅H₁₁ | 742.68 | 68 | 0.58 | −27.8 |
| PFR-ANSNHC₅H₁₁.2HCl | 715.74 | 84 | 0.33 | −33.4 |
| ZGGRR-ANSNH(cyclo-C₆H₁₁) | 864.93 | 68 | 0.45 | −12.2 |
| GGRR-ANSNH(cyclo-C₆H₁₁).3HBr | 993.55 | 79 | 0.36 | +4.2 |
| MesD-LPR-ANSN(C₂H₅)₂ | 682.80 | 87 | 0.62 | −12.9 |
| ZD-LPR-ANSN(CH₂)₅ | 790.98 | 92 | 0.69 | −9.9 |
| D-LPR-ANSN(CH₂)₅.2HBr | 832.00 | 85 | 0.44 | −20.9 |
| (N$^\alpha$-Boc,N$^\omega$-Z)KR-ANSN(CH₃)₂ | 768.93 | 87 | 0.59 | −6.3 |
| (N$^\omega$-Z)KR-ANSN(CH₃)₂.2HCl | 741.73 | 81 | 0.49 | +15.4 |
| KR-ANSN(CH₃)₂.3HBr | 777.43 | 82 | 0.28 | +9.6 |
| BzlGR-ANSNH(i-C₃H₇) | 694.80 | 85 | 0.61 | −19.4 |
| TosGPR-ANSNH(i-C₃H₉) | 742.86 | 75 | 0.61 | −38.0 |

$^a$BAW 412
$^b$Solvent is DMSO.

EXAMPLE 5

Fluorogenic Enzyme Assay

Enzyme assays (except factor VIIa assays, see below) were conducted in 20 mM Tris, 150 mM NaCl, pH 7.4 (TBS) at room temperature (22° C.). The final volume for all reaction mixtures was 2.0 ml. Fluorogenic substrates were dissolved in DMSO to a stock concentration of 10 mM. The 10 mM stock solution was diluted in TBS to the final working concentration prior to all assays. Enzyme was added to mixtures containing buffer components and substrate and the initial rate of substrate hydrolysis was measured as the change in fluorescent intensity over time, corresponding to the generation of the particular 6-amino-1-naphthalenesulfonamide fluorophore from the provided substrate. Quantitation of substrate hydrolysis was accomplished by establishing a standard curve from the appropriate fluorescent moiety. Fluorescence was monitored (continuously or discontinuously) using a Perkin Elmer fluorescence spectrophotometer, model MPF-44A, equipped with a standard chart recorder. The fluorophore was detected using monochrometers set at an excitation wavelength of 352 nm and an emission wavelength of 470 nm. Light scattering artifacts were minimized using a 399 nm cut off filter in the emission light beam.

Data Analysis

The kinetic constants of substrate hydrolysis were determined using the non-linear least squares regression analysis program ENZFITTER (Cambridge, UK). This program was used to iteratively fit initial rates of substrate hydrolysis to the Michaelis-Menten equation and the kinetic constants of substrate hydrolysis (K$_m$) and (k$_{cat}$) were calculated. Data from these assays are shown in Tables 6–9.

TABLE 6

Time (min) for 10% hydrolysis of 6-($N^\alpha$-carbobenzyloxy-L-arginyl)amino-1-naphthalenesulfonamides[c] [($N^\alpha$-Z)ArgANSN$R_1R_2$]

| $R^1$ | $R^2$ | IIa | Xa | APC | Plm | t-PA | u-PA |
|---|---|---|---|---|---|---|---|
| H | $CH_3$ | 38 | 25 | 120 | 1620[b] | 1280[b] | 660 |
| H | $C_2H_5$ | 30 | 25 | 34 | N.D. | 1140[b] | 270 |
| H | $C_3H_7$ | 27 | 40 | 15 | 1620[b] | N.D. | 220 |
| H | i-$C_3H_7$ | 34 | 36 | 50 | 1370[b] | N.D. | 1260 |
| H | $C_4H_9$ | 17 | 34 | 8 | 540 | 720[b] | 28 |
| H | i-$C_4H_9$ | 25 | 33 | 17 | 1620[b] | N.D. | 200 |
| H | t-$C_4H_9$ | 34 | 45 | 45 | 910[b] | N.D. | 1260 |
| H | $C_5H_{11}$ | 30 | 45 | 12 | 510 | 1280[b] | 43 |
| H | cyclo-$C_6H_{11}$ | 23 | 55 | 12 | 1140 | N.D. | 1620[b] |
| H | benzyl | 17 | 46 | 12 | 330 | 510 | 19 |
| $CH_3$ | $CH_3$ | 45 | 15 | 200 | 1140 | N.D. | N.D. |
| $C_2H_5$ | $C_2H_5$ | 165 | 14 | 1080 | 1370[b] | N.D. | N.D. |
| ($CH_2$)$_5$ | | 90 | 41 | 360 | 1220 | N.D. | N.D. |
| ($CH_2$)$_6$ | | 90 | 20 | 813 | 770[b] | N.D. | N.D. |
| morpholyl | | 76 | 45 | 171 | 1220[b] | N.D. | N.D. |

[a] Concentration of Enzyme, 100 nM.
[b] Time (min) for 5% hydrolysis.
[c] Substrate concentration, 1 μM.
N.D. Less than 5% hydrolysis after 24 hrs.

TABLE 7

Hydrolysis Kinetic Constants[a] for 6-($N^\alpha$-carbobenzyloxy-L-arginyl)amino-1-naphthalenesulfonamides ($N^\alpha$-Z)ArgANSN$R_1R_2$

| $R_1$ | $R_2$ | | IIa | Xa | APC |
|---|---|---|---|---|---|
| H | $CH_3$ | $K_m$ | 62.5 | 160 | b |
| | | $k_{cat}$ | 0.04 | 0.11 | |
| | | $k_{cat}/K_m$ | 640 | 714 | |
| H | $C_2H_5$ | $K_m$ | 171 | 121 | b |
| | | $k_{cat}$ | 0.14 | 0.08 | |
| | | $k_{cat}/K_m$ | 820 | 636 | |
| H | $C_3H_7$ | $K_m$ | 22.2 | 125 | 320 |
| | | $k_{cat}$ | 0.04 | 0.07 | 0.47 |
| | | $k_{cat}/K_m$ | 1580 | 593 | 1470 |
| H | i-$C_3H_7$ | $K_m$ | 25 | 102 | 343 |
| | | $k_{cat}$ | 0.03 | 0.08 | 0.17 |
| | | $k_{cat}/K_m$ | 1180 | 800 | 510 |
| H | $C_4H_9$ | $K_m$ | 32.4 | 139 | 171 |
| | | $k_{cat}$ | 0.04 | 0.08 | 0.62 |
| | | $k_{cat}/K_m$ | 1260 | 576 | 3600 |
| H | i-$C_4H_9$ | $K_m$ | 35.3 | 86.5 | 960 |
| | | $k_{cat}$ | 0.05 | 0.07 | 1.6 |
| | | $k_{cat}/K_m$ | 1420 | 811 | 1670 |
| H | t-$C_4H_9$ | $K_m$ | 24 | 114 | 738 |
| | | $k_{cat}$ | 0.02 | 0.06 | 0.4 |
| | | $k_{cat}/K_m$ | 930 | 487 | 540 |
| H | $C_5H_{11}$ | $K_m$ | 41.4 | 36.8 | 436 |
| | | $k_{cat}$ | 0.01 | 0.04 | 0.8 |
| | | $k_{cat}/K_m$ | 242 | 979 | 1830 |
| H | cyclo-$C_6H_{11}$ | $K_m$ | 27.9 | 51.8 | 810 |
| | | $k_{cat}$ | 0.03 | 0.03 | 0.44 |
| | | $k_{cat}/K_m$ | 1090 | 633 | 2470 |
| H | benzyl | $K_m$ | 41 | 213 | 218 |
| | | $k_{cat}$ | 0.07 | 0.04 | 0.23 |
| | | $k_{cat}/K_m$ | 1680 | 198 | 1050 |
| $CH_3$ | $CH_3$ | $K_m$ | 22.6 | 91.4 | b |
| | | $k_{cat}$ | 0.01 | 0.09 | |
| | | $k_{cat}/K_m$ | 630 | 1020 | |
| $C_2H_5$ | $C_2H_5$ | $K_m$ | b | 200 | |
| | | $k_{cat}$ | | 0.26 | |
| | | $k_{cat}/K_m$ | | 1290 | |
| ($CH_2$)$_5$ | | $K_m$ | b | 64.9 | b |
| | | $k_{cat}$ | | 0.06 | |
| | | $k_{cat}/K_m$ | | 924 | |
| ($CH_2$)$_6$ | | $K_m$ | b | 427 | b |
| | | $k_{cat}$ | | 0.13 | |
| | | $k_{cat}/K_m$ | | 293 | |
| morpholyl | | $K_m$ | b | 80 | b |
| | | $k_{cat}$ | | 0.05 | |
| | | $k_{cat}/K_m$ | | 625 | |

[a] $K_m$ = μM, $k_{cat}$ = sec$^{-1}$, $k_{cat}/K_m$ = sec$^{-1}$M$^{-1}$.
[b] Slow substrate hydrolysis, no kinetic constants calculated.

TABLE 8

Relative hydrolysis rates of 6-peptidylamino-1-naphthalenesulfonamide substrates for various serine protease enzymes.

| Substrates | IIa[a] | Plm[a] | VIIa[a] | IXa[b] | Xa[a] | APC[a] | u-PA[b] | t-PA[b] |
|---|---|---|---|---|---|---|---|---|
| BocPFR-ANSNH$C_3H_7$ | 4 | 22 | d | d | 9 | 3 | 5 | 4 |
| PFR-ANSNH$C_3H_7$ | 5 | 13 | d | d | 1.25 | 0.25 | 6 | d |
| BocPPR-ANSNH$C_5H_{11}$ | 0.03 | 8[b] | d | d | 27[b] | 2.5 | 0.65 | 70 |
| PPR-ANSNH$C_5H_{11}$ | 0.06 | 3[b] | d | d | 40[b] | 0.25 | 0.5 | 40 |
| ZGGRR-ANSNH (cyclo-$C_6H_{11}$) | 93 | 47 | d | d | d | 0.6 | d | d |
| GGRR-ANSNH (cyclo-$C_6H_{11}$) | 93 | 2.5[b] | d | d | 46[b] | 0.5 | 24 | d |
| MesD-LPR-ANSN ($C_2H_5$)$_2$ | 0.33 | 1 | 4 | 33 | 0.01 | 0.5[b] | 2 | 2 |
| ZD-LPR-ANSN($CH_2$)$_5$ | 0.01[c] | 0.08 | d | 7 | 0.02 | 0.5 | 1 | 1 |
| D-LPR-ANSN($CH_2$)$_5$ | 0.01[c] | 0.33 | d | 4 | 0.4 | 0.02 | 1 | 1.3 |
| ($N^\alpha$-Boc,$N^\bullet$-Z)KR-ANSN($CH_{23}$)$_2$ | 18 | 1.5[b] | d | d | 24[b] | 11[b] | d | d |
| $N^\omega$-AZ)KJR-ANSN($CH_3$)$_2$ | 26 | 1.5[b] | d | d | d | 5.5[b] | d | d |
| KR-ANSN($CH_3$)$_2$ | d | 8[b] | d | d | d | 8[b] | d | d |
| BzlGR-ANSNH (i-$C_3H_7$) | 0.4 | 2[b] | d | d | 0.45 | 6 | 2 | 6 |
| TosGPR-ANSNH (i-$C_4H_9$) | 0.01[c] | 0.25 | d | 42 | 0.05 | 0.02 | 0.01 | 2 |

[a] 10 nM enzyme
[b] 100 nM enzyme
[c] 1 nM enzyme
[d] hydrolysis at 100 hours was less than 10%.
Substrate concentration: 1 μM.

TABLE 9

Kinetic constants[a] for hydrolysis of 6-peptidylamino-1-naphthalenesulfonamide substrates

| Substrates | Kinetic Contstants | IIa | Xa | IXa | APC |
|---|---|---|---|---|---|
| BocPFR-ANSNHC$_3$H$_7$ | kcat | 0.04 | 0.06 | b | b |
|  | Km | 44.4 | 230 |  |  |
|  | kcat/km | 900 | 260 |  |  |
| PFR-ANSNHC$_3$H$_7$ | kcat | 0.36 | 1.33 | b | 4.7 |
|  | Km | 600 | 667 |  | 240 |
|  | kcat/Km | 600 | 2000 |  | 19600 |
| BocPPR-ANSNHC$_5$H$_{11}$ | kcat | 1.39 | b | b | b |
|  | Km | 10.9 |  |  |  |
|  | kcat/Km | 12800 |  |  |  |
| PPR-ANSNHC$_5$H$_{11}$ | kcat | 30.3 | b | b | 14.3 |
|  | Km | 667 |  |  | 640 |
|  | kcat/Km | 45000 |  |  | 22300 |
| ZGGRR-ANSNH (cyclo-C$_6$H$_{11}$) | kcat | b | b | b | 6.2 |
|  | Km |  |  |  | 320 |
|  | kcat/Km |  |  |  | 19300 |
| GGRR-ANSNH (cyclo-C$_6$H$_{11}$) | kcat | b | b | b | 3.1 |
|  | Km |  |  |  | 267 |
|  | kcat/Km |  |  |  | 11600 |
| MesD-LPR-ANSN (C$_2$H$_5$)$_2$ | kcat | 0.63 | 36.4 | 0.033 | b |
|  | Km | 31.6 | 12.5 | 96 |  |
|  | kcat/Km | 20000 | 291000 | 347 |  |
| ZD-LPR-ANSN(CH$_2$)$_5$ | kcat | 16.1 | 3.5 | 0.39 | 7.1 |
|  | Km | 4.2 | 26.3 | 141 | 246 |
|  | kcat/Km | 3.8 × 10$^4$ | 133000 | 2750 | 28900 |
| D-LPR-ANSN(CH$_2$)$_5$ | kcat | 11.6 | 2.9 | 0.4 | 1.1 |
|  | Km | 7.7 | 400 | 343 | 160 |
|  | kcat/Km | 1.5 × 10$^6$ | 7250 | 1170 | 6880 |
| BzlGR-ANSNH (i-C$_3$H$_7$) | kcat | 1.8 | 0.44 | b | b |
|  | Km | 320 | 55.2 |  |  |
|  | kcat/Km | 5600 | 7970 |  |  |
| TosGPR-ANSNH (i-C$_4$H$_9$) | kcat | 52.6 | 2.4 | 0.3 | 120 |
|  | Km | 11 | 35.3 | 123 | 800 |
|  | kcat/Km | 4.8 × 10$^6$ | 6800 | 2400 | 150000 |

[a] $K_m = \mu M$, $k_{cat} = sec^{-1}$, $k_{cat}/k_m = sec^{-1}M^{-1}$
[b] slow substrate hydrolysis, no kinetic constants calculated.

EXAMPLE 6

Fluorogenic Factor VIIa Assay

Factor VII assays were conducted in 20 mM HEPES, 150 mM NaCl, 5 mM CaCl$_2$, pH 7.4 (HBS) at 37° C. The final volume for all reactions was 1.6 ml. 6-(Mes-D-Leu-Gly-Arg)amino-1-(N,N-diethyl)naphthalenesulfonamide was dissolved in DMSO to a stock concentration of 10 mM. This 10 mM stock solution of was diluted in HBS to final working concentration prior to all assays. For reactions involving tissue factor (TF) and phospholipid vesicles, recombinant human tissue factor was solubilized in either 0.04% n-dodecyl octaethylene glycol (C$_{12}$E$_8$) or 0.8% octyl glucoside. The TF/n-dodecyl octaethylene glycol was then relipidated into PCPS or PC vesicles by a 30 minute incubation step as described by Lawson & Mann, J. Biol. Chem. 266: 11317–11327 (1991). TF/octyl glucoside was relipidated into PC or PCPS vesicles by a thirty minute incubation step followed by exhaustive dialysis. The final concentration of tissue factor used in the studies described here ranged from 2 to 50 nM depending on the nature of the experiment.

Fifteen minutes prior to the start of all reactions factor VIIa was added to the reaction system. This incubation period was followed by the addition of substrate (1 $\mu M$ to 400 $\mu M$) to the mixture to start the reaction. In experiments designed to determine kinetic constants of substrate hydrolysis, 50 nM rVIIa was used when no tissue factor was present in the reaction system, while 0.5 nM rVIIa was used when tissue factor was present in the reaction system. The rate of substrate hydrolysis was measured by change in fluorescence over time, which corresponded with the generation of the 6-amino-1-(N,N-diethyl)naphthalenesulfonamide from the provided substrate. The kinetic constants of 6-(Mes-D-Leu-Gly-Arg)amino-1-(N,N-diethyl)naphthalenesulfonamide hydrolysis as a function of factor VIIa/tissue factor complex assembly are shown in Table 10.

TABLE 10

| Enzyme | $K_m$ $\mu M$ ± S.E. | $k_{cat}$ sec$^{-1}$ ± S.E. | $k_{cat}/K_m$ M$^{-1}$s$^{-1}$ |
|---|---|---|---|
| VIIa/Ca$^{2+}$ | 249 ± 88.5 | 0.010 ± 0.002 | 41.4 |
| VIIa/PCPS/Ca$^{2+}$ | 580 ± 101 | 0.019 ± 0.003 | 32.6 |
| VIIa/TF/PCPS/Ca$^{2+}$ | 162 ± 16 | 0.675 ± 0.046 | 4166 |
| VIIa/TF/PC/CA$^{2+}$ | 208 ± 12 | 0.875 ± 0.032 | 4206 |

The data in Table 10 indicate that in a mixture composed of equal amounts of bound (factor VII complexed to tissue factor) and free factor VIIa, the free factor VIIa would contribute less than one percent to the observed rate of substrate hydrolysis.

Proteolytic Release of 6-Amino-1-(diethyl)naphthalenesulfonamide Fluorescent Product from Peptidyl Substrate A factor VII assay was conducted using 2 nM factor VIIa, 200 $\mu M$ PCPS, and 40 $\mu M$ 6-(Mes-D-Leu-Gly-Arg)amino-1-(diethyl)naphthalenesulfonamide. The reagents were incubated at 37° C. for 10 min, after which 25 mM EDTA was added to the reaction to block further substrate hydrolysis. To the assay mixture was then added 0.5 nM human thrombin (IIa). The change in fluorescence was plotted as a function of time. The results are shown in the direct tracing of FIG.

1 which illustrates that the increase in factor VIIa substrate hydrolysis in the presence of tissue factor is Ca$^{2+}$ dependent and that the addition of EDTA to the reaction system did not directly effect the substrate or fluorescent detection system, which are still reactive with thrombin.

Binding of Factor VIIa to Tissue Factor

The binding of factor VIIa to tissue factor was analyzed by factor VIIa substrate hydrolysis when complexed with tissue factor. Tissue factor was relipidated into PC or PCPS vesicles as described above. The final concentration of tissue factor and phospholipid used for all binding studies was 2 nM and 200 μM respectively. In control experiments where tissue factor was in excess, 50 nM tissue factor and 200 μM PCPS vesicles were used. Recombinant factor VIIa (0.5 to 20 nM) was added to assembled TF/phospholipid complex and incubated for 15 minutes at 37° C. in HBS. The reaction was started by the addition of substrate (40 μM final) and the rate of substrate hydrolysis as reported by an increase in fluorescent intensity was recorded as described above in Example 5. The instrument was standardized daily using a 1 μM stock of the 6-amino-1-(N,N-diethyl)napthalenesulfonamide in HBS at 37° C. as described above.

The apparent dissociation constant of factor VIIa binding to tissue factor was determined kinetically by measuring the rate of 6-(Mes-D-Leu-Gly-Arg)amino-1-(N,N-diethyl)naphthalenesulfonamide hydrolysis as a function of increasing factor VIIa concentrations over a fixed concentration of tissue factor. The presumed bound concentration of factor VIIa was determined by calculating the amount of factor VIIa (complexed to tissue factor) that would produce the observed rate of substrate hydrolysis. Free ligand was determined by the difference between the calculated amount of bound ligand and the total amount of ligand added. Binding data were evaluated using the non-linear least square regression program ENZFITTER.

The dissociation constant ($K_d$) and binding stoichiometry (n) were calculated from the best fit line, assuming one class of high affinity binding sites. The binding constants determined using the above described assay are shown in Table 11.

TABLE 11

| Enzyme Complex | $K_d$ | n |
| --- | --- | --- |
| TF/PC | 1.13 +/− 0.28 | 1.04 +/− 0.10 |
| TF/PCPS | 2.09 +/− 0.53 | 1.06 +/− 0.12 |

$K_d$ = nM; n = moles of factor VIIa bound per mole of TF.

Figure 2:
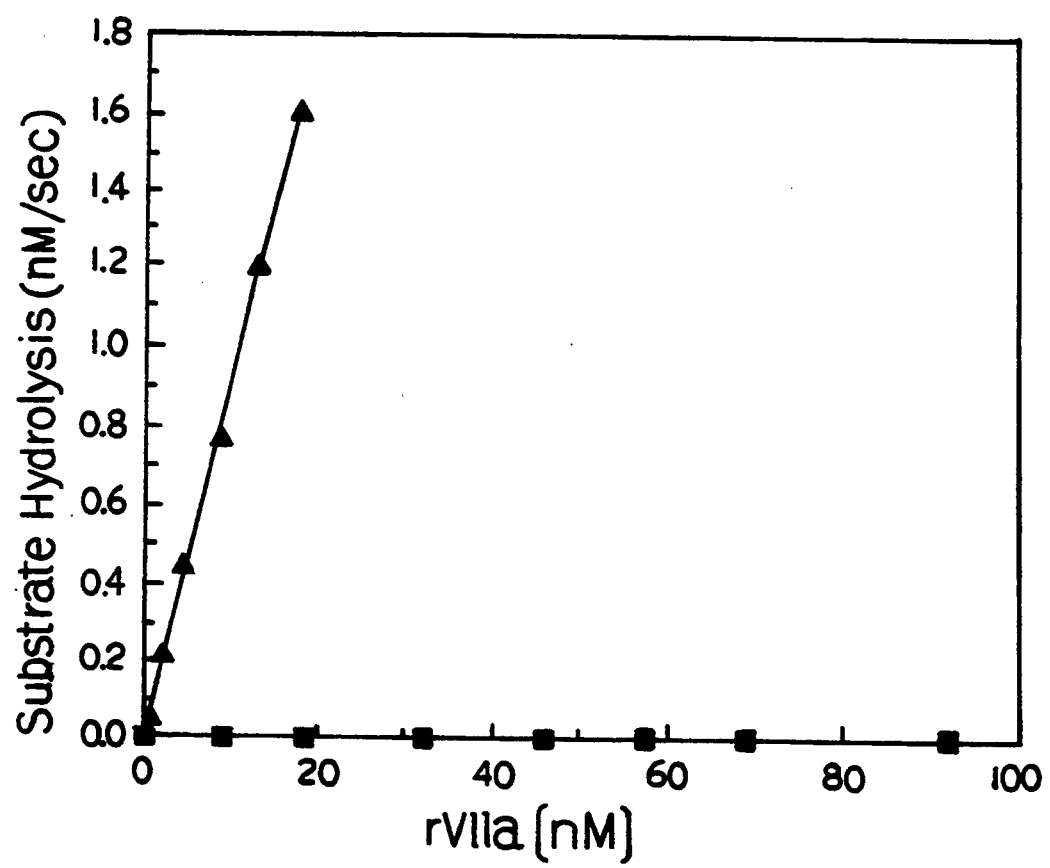
FIG. 2 is a graph of the rate of factor VIIa substrate [6-(Mes-D-Leu-Gly-Arg)amino-1-(diethyl)naphthalenesulfonamide]hydrolysis in the presence and absence of tissue factor. The filled squares represent the rate of substrate hydrolysis as a function of increasing factor VIIa in HEPES buffered saline (HBS). Filled triangles represent the rate of substrate hydrolysis as a function of increasing factor VIIa concentrations with an excess of tissue factor (TF) (50 nM) in the experimental system.

The increase in the rate of factor VIIa substrate hydrolysis, both in the presence and absence of tissue factor, is linear over the concentration range tested, as shown in FIG. 2. In addition, FIG. 2 illustrates that tissue factor dramatically enhanced (>100 fold) the rate of factor VIIa substrate hydrolysis. In FIG. 2, filled triangles represent the rate of substrate hydrolysis as a function of increasing factor VIIa concentrations with an excess of tissue factor (50 mM) in the assay. Filled squares represent the rate of factor VIIa substrate hydrolysis on the absence of tissue factor. The substrate concentration employed in the rate determination experiments was 40 μM.

Figure 3:
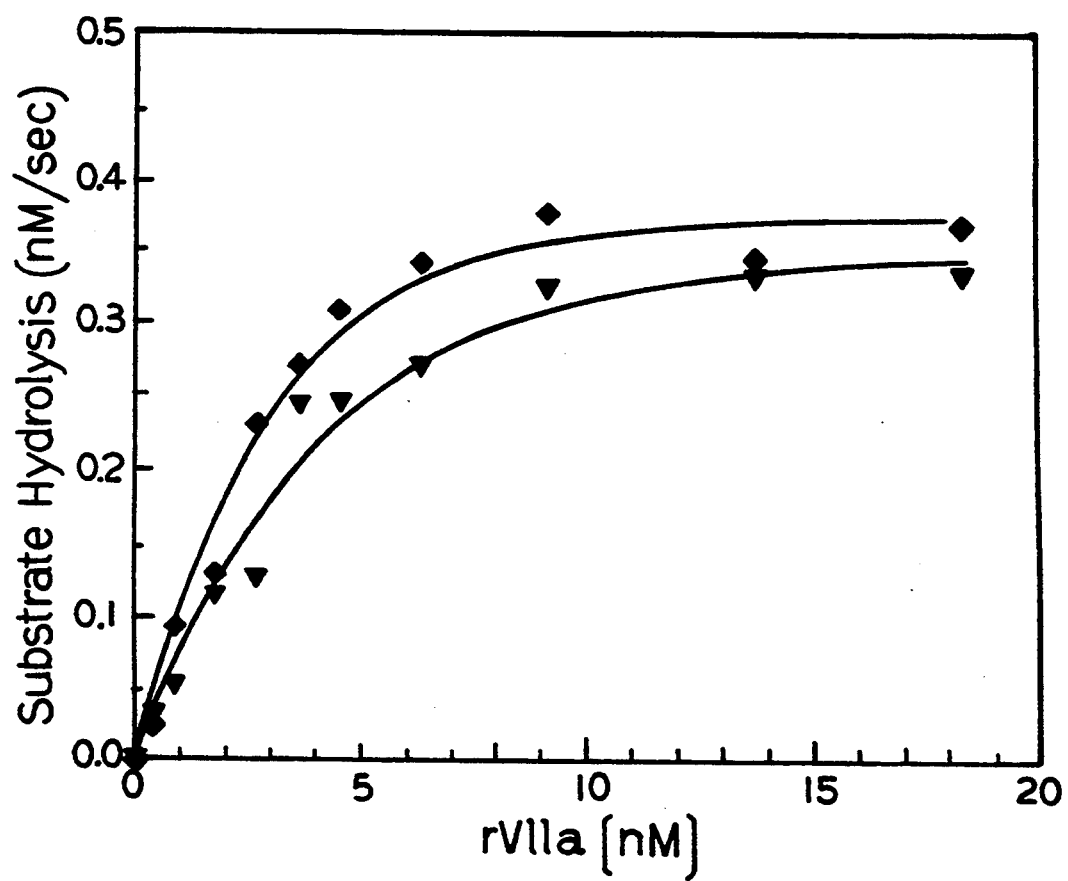
FIG. 3 is a graph showing the binding of factor VIIa to tissue factor containing phospholipid vesicles as measured by substrate [6-(Mes-D-Leu-Gly-Arg)amino-1-(diethyl)naphthalenesulfonamide]hydrolysis. Filled diamonds represent the binding of factor VIIa to TF/PC vesicles while filled triangles represents the binding to factor VIIa to TF/PCPS vesicles.

When tissue factor was the limiting reagent in the reaction (tissue factor concentration: 2.8 nM), the rate of factor VIIa-dependent substrate hydrolysis is initially factor VIIa-dependent and then saturates at factor VIIa concentrations between 3 and 7 nM, as shown in FIG. 3.

These data provide compelling evidence that the enhanced rate of substrate hydrolysis is directly related to factor VIIa and its binding to tissue factor and is not caused by a contaminating protease in the factor VIIa preparation which would function independently of tissue factor. In addition, the amount of factor VIIa, which was bound to either tissue factor/PC or tissue factor/PCPS vesicles, was inferred from the kinetic constants reported in Table 10 above and the data presented in FIG. 3.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

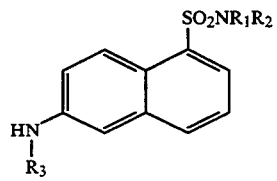

and the pharmaceutically acceptable non-toxic salts thereof; wherein $R_1$ is hydrogen, straight or branched chain lower alkyl having 1-6 carbon atoms, straight or branched chain alkenyl having 2-8 carbon atoms, straight or branched chain alkynyl having 2-8 carbon atoms, cycloalkyl having 3-7 carbon atoms, alkylcycloalkyl where the alkyl portion has 1-6 carbon atoms, cycloalkylalkyl where the alkyl portion has 1-6 carbon atoms, or phenylalkyl where the alkyl portion is straight or branched chain alkyl having 1-6 carbon atoms, or a group of the formula

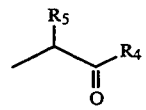

wherein $R_5$ represents an amino acid side chain and $R_4$ is hydroxy, an amino acid or a peptide residue;

$R_2$ is hydrogen, straight or branched chain lower alkyl having 1-6 carbon atoms, straight or branched chain alkenyl having 2-8 carbon atoms, straight or branched chain alkynyl having 2-8 carbon atoms, cycloalkyl having 3-7 carbon atoms, alkylcycloalkyl where the alkyl portion has 1-6 carbon atoms, cycloalkylalkyl where the alkyl portion has 1-6 carbon atoms, or phenylalkyl where the alkyl portion is straight or branched chain alkyl having 1-6 carbon atoms, or a group of the formula

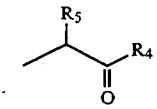

wherein $R_5$ represents an amino acid side chain and $R_4$ is hydroxy, an amino acid or a peptide residue; or $NR_1R_2$ forms a nitrogen heterocycle; and $R_3$ is an amino acid or a peptide residue.

2. A compound according to claim 1, wherein $R_3$ is lysine or arginine.

3. A compound according to claim 1, where $R_3$ is a peptide having arginine or lysine at the carboxy terminus.

4. A compound according to claim 3, which is 6-L-arginylamino-1-(N-ethyl)naphthalenesulfonamide.

5. A compound according to claim 3, which is 6-L-arginylamino-1-(N-n-propyl)naphthalenesulfonamide.

6. A compound according to claim 3, which is 6-L-arginylamino-1-(N-isopropyl)naphthalenesulfonamide.

7. A compound according to claim 3, which is 6-L-arginylamino-1-(N-n-butyl)naphthalenesulfonamide.

8. A compound according to claim 3, which is 6-L-arginylamino-1-(N-isobutyl)naphthalenesulfonamide.

9. A compound according to claim 3, which is 6-L-arginylamino-1-(N-tert-butyl)naphthalenesulfonamide.

10. A compound according to claim 3, which is 6-L-arginylamino-1-(N-n-pentyl)naphthalenesulfonamide.

11. A compound according to claim 3, which is 6-L-arginylamino-1-(N-cyclohexyl)naphthalenesulfonamide.

12. A compound according to claim 3, which is 6-L-arginylamino-1-(N-benzyl)naphthalenesulfonamide.

13. A compound according to claim 3, which is 6-L-arginylamino-1-(N,N-diethyl)naphthalenesulfonamide.

14. A compound according to claim 3, which is 1-[(6-L-arginylamino-1-naphthalenyl)sulfonyl]-piperidine.

15. A compound according to claim 3, which is 1-[(6-L-arginylamino-1-naphthalenyl)sulfonyl]-morpholine.

16. A compound according to claim 3, which is 1[(6-L-arginylamino-1-naphthalenyl)sulfonyl]-pyrrolidine.

17. A compound according to claim 3, which is 6-L-arginylamino-1-(N,N-dimethyl)naphthalenesulfonamide.

18. A compound according to claim 3, which is 6-L-arginylamino-1-(N-methyl)naphthalenesulfonamide.

19. A compound according to claim 3, which is 6-(t-butoxycarbonyl-prolyl-phenylalanyl-arginylamino)-1-(N-n-propyl)naphthalenesulfonamide.

20. A compound according to claim 3, which is 6-(prolyl-phenylalanyl-arginylamino)-1-(N-n-propyl)-naphthalenesulfonamide.

21. A compound according to claim 3, which is 6-(t-butoxycarbonyl-phenylalanyl-phenylalanyl-arginylamino)-1-(N-n-pentyl)naphthalenesulfonamide.

22. A compound according to claim 3, which is 6-(phenylalanyl-phenylalanyl-arginylamino)-1-(N-n-pentyl)naphthalenesulfonamide.

23. A compound according to claim 3, which is 6-(carbobenzyloxy-glycyl-glycyl-arginyl-arginylamino)-1-(N-cyclohexyl)naphthalenes 24. A compound according to claim 3, which is 6-(glycyl-glycyl-arginyl-arginylamino)-1-(N-cyclohexyl)-naphthalenesulfonamide.

25. A compound according to claim 3, which is 1-[(6-methanesulfonyl-D-leucinyl-phenylalanyl-arginylamino-1naphthalenyl)sulfonyl]-piperidine.

26. A compound according to claim 3, which is 1[(6-benzyloxycarbonyl-D-leucinyl-phenylalanyl-arginylamino-1-naphthalenyl)sulfonyl]-piperidine.

27. A compound according to claim 3, which is 1-[(6-D-leucinyl-phenylalanyl-arginylamino-1-naphthalenyl)sulfonyl]-piperidine.

28. A compound according to claim 3, which is 6-($N^\alpha$-t-butoxycarbonyl, $N_\omega$-benzyloxycarbonyl-lysylarginylamino)-1-(N,N-dimethyl)naphthalenesulfonamide.

29. A compound according to claim 3, which is 6-($N^{107}$-benzyloxycarbonyl-lysyl-arginylamino)-1-(N,N-dimethyl)-1-naphthalenesulfonamide.

30. A compound according to claim 3, which is 6lysyl-arginylamino)-1-(N,N-dimethyl)napthalenesulfonamide.

31. A compound according to claim 3, which is 6(benzoyl-isoleucinyl-glycinyl-arginylamino)-1-(N-isopropyl)napthalenesulfonamide.

32. A compound according to claim 3, which is 6-(toluenesulfonyl-glycyl-phenylalanyl-arginylamino)-1-(N-isobutyl)naphthalenesulfonamide.

33. A compound according to claim 3, which is 6-(methanesulfonyl-D-leucinyl-glycinyl-arginylamino)-1-(N,N-diethyl)naphthalenesulfonamide.

34. A method for determining proteolytic enzyme activity comprising the steps of:

(a) contacting a proteolytic enzyme with a substrate compound of the formula:

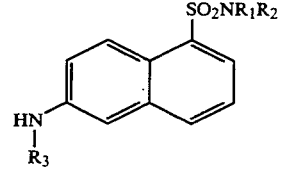

wherein
$R_1$ is hydrogen, straight or branched chain lower alkyl having 1-6 carbon atoms, straight or branched chain alkenyl having 2-8 carbon atoms, straight or branched chain alkynyl having 2-8 carbon atoms, cycloalkyl having 3-7 carbon atoms, alkylcycloalkyl where the alkyl portion has 1-6 carbon atoms, cycloalkylalkyl where the alkyl portion has 1-6 carbon atoms, or phenylalkyl where the alkyl portion is straight or branched chain alkyl having 1-6 carbon atoms, or a group of the formula

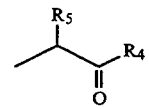

wherein $R_5$ represents an amino acid side chain and $R_2$ is hydroxy, an amino acid or a peptide residue;

$R_2$ is hydrogen, straight or branched chain lower alkyl having 1-6 carbon atoms, straight or branched chain alkenyl having 2-8 carbon atoms, straight or branched chain alkynyl having 2-8 carbon atoms, cycloalkyl having 3-7 carbon atoms, alkylcycloalkyl where the alkyl portion has 1-6 carbon atoms, cycloalkylalkyl where the alkyl portion has 1–6 carbon atoms, or phenylalkyl where the alkyl portion is straight or branched chain alkyl having 1–6 carbon atoms, or a group of the formula

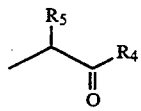

wherein $R_5$ represents an amino acid side chain and $R_4$ is hydroxy, an amino acid or a peptide residue; or $NR_1R_2$ forms a nitrogen heterocycle; and $R_3$ is an amino acid or a peptide residue; and (b) measuring fluorescence intensity changes as a result of substrate compound hydrolysis.

35. A method according to claim 34, where $R_3$ is lysine or arginine.

36. A method according to claim 34, where $R_3$ is a peptide having arginine or lysine at the carboxy terminus.

37. A method according to claim 36, wherein the proteolytic enzyme is a serine protease involved in blood coagulation.

38. A method according to claim 34, wherein the proteolytic enzyme is factor VIIa, tissue plasminogen activator, urokinase, factor IIa, factor IXa, factor Xa, plasmin, or activated protein C.

* * * * *

UNITED STATES PATENT AND TRADEMARK OFFICE
CERTIFICATE OF CORRECTION

PATENT NO. : 5,399,487
DATED : March 21, 1995
INVENTOR(S) : Butenas et al.

It is certified that error appears in the above-indentified patent and that said Letters Patent is hereby corrected as shown below:

At column 1, line, 7, below "Background of the Invention" insert the following Paragraph:

This invention was made pursuant to Grant No. PO1 HL46703 from the National Institute of Health, United States of America. Thus, the Government may have certain rights in the inventions.

Signed and Sealed this

First Day of October, 1996

Attest:

BRUCE LEHMAN

Attesting Officer

Commissioner of Patents and Trademarks